(12) United States Patent
Marici et al.

(10) Patent No.: US 12,098,785 B2
(45) Date of Patent: *Sep. 24, 2024

(54) UNIVERSAL CONNECTOR OR CAP FOR MALE AND FEMALE THREADED FITTINGS

(71) Applicant: Becton, Dickinson and Company, Franklin Lakes, NJ (US)

(72) Inventors: Paul P. Marici, Piscataway, NJ (US); Kevin M. Ryan, Whitehouse Station, NJ (US); Chang Jiang, Butler, NJ (US); Michael Kwong Chan, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 34 days.

This patent is subject to a terminal disclaimer.

(21) Appl. No.: 17/730,927

(22) Filed: Apr. 27, 2022

(65) Prior Publication Data

US 2022/0252189 A1    Aug. 11, 2022

Related U.S. Application Data

(63) Continuation of application No. 17/076,102, filed on Oct. 21, 2020, now Pat. No. 11,353,147, which is a
(Continued)

(51) Int. Cl.
*F16L 15/06* (2006.01)
*A61M 39/16* (2006.01)
(Continued)

(52) U.S. Cl.
CPC ............ *F16L 15/06* (2013.01); *A61M 39/165* (2013.01); *A61M 39/20* (2013.01); *F16L 15/002* (2013.01); *B65D 41/04* (2013.01)

(58) Field of Classification Search
CPC ...... A61M 39/00; A61M 39/10; A61M 39/16; A61M 39/165; A61M 39/20;
(Continued)

(56) References Cited

U.S. PATENT DOCUMENTS 3,403,679 A    10/1968 Sinclair et al.
4,417,890 A    11/1983 Dennehey et al.
(Continued)

FOREIGN PATENT DOCUMENTS

CA    2523133 C    2/2013
CN    101980746 A    2/2011
(Continued)

OTHER PUBLICATIONS

"Final Office Action in U.S. Appl. No. 16/253,683 dated Dec. 23, 2020, 9 pages".
(Continued)

*Primary Examiner* — Natasha E Young
(74) *Attorney, Agent, or Firm* — Servilla Whitney LLC

(57) ABSTRACT

A cap is described for connection to a medical connector, the cap includes a housing having a top wall and sidewall forming a first cavity, and a removable or integrally formed protrusion. The protrusion includes an inner thread on an inner surface, the inner thread being sufficient to interlock with a mating feature of a female needleless connector. The inner surface of the protrusion defines a second cavity. The protrusion includes an outer thread on an outer surface, the outer thread being sufficient to interlock with a mating feature of a male needleless connector. The second cavity configured to define a chamber to contain an absorbent material and disinfectant or antimicrobial agent. The cap may also include a peel seal and/or septum to prevent the disinfectant or the antimicrobial agent from exiting the
(Continued)

second cavity. An exterior sidewall surface of the housing may include a plurality of grip members.

21 Claims, 34 Drawing Sheets

Related U.S. Application Data continuation of application No. 16/261,761, filed on Jan. 30, 2019, now Pat. No. 10,871,246.

(60) Provisional application No. 62/623,858, filed on Jan. 30, 2018.

(51) Int. Cl.
*A61M 39/20* (2006.01)
*B65D 41/04* (2006.01)
*F16L 15/00* (2006.01)

(58) Field of Classification Search
CPC .......... A61M 2039/00; A61M 2039/10; A61M 2039/1033; B65D 41/00; B65D 41/02; B65D 41/04; F16L 15/00; F16L 15/001; F16L 15/002; F16L 15/06
See application file for complete search history.

(56) References Cited

U.S. PATENT DOCUMENTS

| | | | |
|---|---|---|---|
| 4,597,758 A | 7/1986 | Aalto et al. | |
| 4,711,363 A | 12/1987 | Marino | |
| 4,738,376 A | 4/1988 | Markus | |
| 5,496,288 A | 3/1996 | Sweeny | |
| 5,676,406 A | 10/1997 | Simmons et al. | |
| 5,755,696 A | 5/1998 | Caizza | |
| 6,632,199 B1 | 10/2003 | Tucker et al. | |
| 7,083,605 B2 | 8/2006 | Miyahara | |
| 8,388,894 B2 | 3/2013 | Colantonio | |
| 8,647,308 B2 | 2/2014 | Solomon et al. | |
| 8,715,231 B2 | 5/2014 | Woehr | |
| 8,721,627 B2 | 5/2014 | Alpert et al. | |
| 8,777,504 B2 | 7/2014 | Shaw et al. | |
| 8,961,475 B2 | 2/2015 | Solomon et al. | |
| 9,039,989 B2 | 3/2015 | Lui et al. | |
| 9,132,223 B1 | 9/2015 | Wakeel | |
| 9,192,449 B2 | 11/2015 | Kerr et al. | |
| 10,099,048 B2 | 10/2018 | Chiu et al. | |
| 10,166,381 B2 | 1/2019 | Gardner et al. | |
| 10,376,686 B2 | 8/2019 | Burkholz et al. | |
| 10,589,080 B2 | 3/2020 | Hitchcock et al. | |
| 10,603,481 B2 | 3/2020 | Avula et al. | |
| 10,871,246 B2 * | 12/2020 | Marici .................. F16L 15/06 | |
| 11,353,147 B2 * | 6/2022 | Marici .................. F16L 15/002 | |
| 11,511,100 B2 * | 11/2022 | Ryan ..................... A01N 47/44 | |
| 11,628,288 B1 | 4/2023 | Solomon et al. | |
| 2003/0209681 A1 | 11/2003 | Leinsing et al. | |
| 2004/0039341 A1 | 2/2004 | Ranalletta | |
| 2004/0044318 A1 | 3/2004 | Fiser et al. | |
| 2005/0147525 A1 | 7/2005 | Bousquet | |
| 2005/0197646 A1 | 9/2005 | Connell et al. | |
| 2007/0060904 A1 | 3/2007 | Vedrine et al. | |
| 2008/0010766 A1 | 1/2008 | Kaufman et al. | |
| 2008/0177250 A1 | 7/2008 | Howlett et al. | |
| 2010/0000040 A1 | 1/2010 | Shaw et al. | |
| 2010/0003067 A1 | 1/2010 | Shaw et al. | |
| 2010/0049170 A1 | 2/2010 | Solomon et al. | |
| 2010/0050351 A1 | 3/2010 | Colantonio et al. | |
| 2010/0100056 A1 | 4/2010 | Cawthon et al. | |
| 2011/0046603 A1 | 2/2011 | Felsovalyi et al. | |
| 2011/0054440 A1 | 3/2011 | Lewis | |
| 2011/0264037 A1 | 10/2011 | Foshee et al. | |
| 2012/0039764 A1 | 2/2012 | Solomon et al. | |
| 2012/0111368 A1 | 5/2012 | Rahimy et al. | |
| 2012/0123386 A1 | 5/2012 | Tsals | |
| 2012/0265163 A1 | 10/2012 | Cheng et al. | |
| 2012/0302997 A1 | 11/2012 | Gardner et al. | |
| 2013/0085474 A1 | 4/2013 | Charles et al. | |
| 2013/0171030 A1 | 7/2013 | Ferlic et al. | |
| 2013/0197485 A1 | 8/2013 | Gardner et al. | |
| 2013/0338644 A1 | 12/2013 | Solomon et al. | |
| 2014/0052074 A1 | 2/2014 | Tekeste | |
| 2014/0150832 A1 | 6/2014 | Rogers et al. | |
| 2014/0366914 A1 | 12/2014 | Kerr et al. | |
| 2015/0011936 A1 | 1/2015 | Okihara et al. | |
| 2015/0094666 A1 | 4/2015 | Bates et al. | |
| 2016/0045629 A1 | 2/2016 | Gardner et al. | |
| 2016/0067422 A1 | 3/2016 | Davis et al. | |
| 2016/0158520 A1 | 6/2016 | Ma et al. | |
| 2017/0203092 A1 | 7/2017 | Ryan et al. | |
| 2018/0085568 A1 | 3/2018 | Drmanovic | |
| 2018/0200145 A1 | 7/2018 | Sanders et al. | |
| 2018/0200500 A1 | 7/2018 | Ziebol et al. | |
| 2018/0214684 A1 | 8/2018 | Avula et al. | |
| 2018/0243547 A1 | 8/2018 | Fox et al. | |
| 2018/0256879 A1 | 9/2018 | Chiu et al. | |
| 2018/0256883 A1 | 9/2018 | Follman et al. | |
| 2019/0001115 A1 | 1/2019 | Ma et al. | |
| 2019/0151643 A1 | 5/2019 | Alpert | |
| 2019/0234540 A1 | 8/2019 | Marici et al. | |
| 2019/0308006 A1 | 10/2019 | Erekovcanski et al. | |
| 2019/0351212 A1 | 11/2019 | Dudar et al. | |
| 2020/0147360 A1 | 5/2020 | Arnett et al. | |
| 2020/0238070 A1 | 7/2020 | Ryan | |
| 2021/0100996 A1 | 4/2021 | Wijesuriya et al. | |
| 2021/0187267 A1 * | 6/2021 | Jiang .................. A61M 39/162 | |
| 2022/0273931 A1 * | 9/2022 | Jiang .................. A61M 39/162 | |
| 2023/0080687 A1 * | 3/2023 | Ryan ..................... A01N 47/44 604/535 | |

FOREIGN PATENT DOCUMENTS

| | | |
|---|---|---|
| CN | 102448502 A | 5/2012 |
| CN | 204161736 U | 2/2015 |
| CN | 216022674 U | 3/2022 |
| CN | 110090354 B | 1/2023 |
| DE | 20017013 U1 | 12/2000 |
| DE | 10247963 A1 | 5/2004 |
| EP | 2606930 A1 | 6/2013 |
| EP | 2832391 B1 | 1/2018 |
| EP | 3275490 A1 | 1/2018 |
| GB | 2408259 A | 5/2005 |
| GB | 2518646 A | 4/2015 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008253775 A | 10/2008 |
| JP | 2009526241 A | 7/2009 |
| JP | 2010527276 A | 8/2010 |
| JP | 2012522593 A | 9/2012 |
| JP | 2014528288 A | 10/2014 |
| JP | 2015517377 A | 6/2015 |
| JP | 2016511111 A | 4/2016 |
| JP | 2016511119 A | 4/2016 |
| JP | 2016104214 A | 6/2016 |
| JP | 7419237 B2 | 1/2024 |
| WO | 200024442 A1 | 5/2000 |
| WO | 200224551 A1 | 3/2002 |
| WO | 2011066586 A1 | 6/2011 |
| WO | 2012144026 A1 | 10/2012 |
| WO | 2014159346 A1 | 10/2014 |
| WO | 2015127285 A1 | 8/2015 |
| WO | 2015174953 A1 | 11/2015 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019147906 A1 | 8/2019 |
| WO | 2019152482 A1 | 8/2019 |

(56) References Cited

FOREIGN PATENT DOCUMENTS

| WO | 2019212637 | A1 | 11/2019 |
|---|---|---|---|
| WO | 2020112767 | A1 | 6/2020 |

OTHER PUBLICATIONS

"Final Office Action in U.S. Appl. No. 16/254,747, mailed on Jan. 22, 2021, 15 pages".
"International Search Report in PCT/US2019/015789, mailed Apr. 16, 2019, 12 pages".
"Non-Final Office Action in U.S. Appl. No. 16/378,015, mailed Mar. 30, 2021, 10 pages".
"Non-Final Office Action in U.S. Appl. No. 16/253,683, mailed on Jun. 26, 2020, 9 pages".
"Non-Final Office Action in U.S. Appl. No. 16/378,015, mailed on Oct. 30, 2020, 18 pages".
"Non-Final Office Action in U.S. Appl. No. 16/838,461, mailed on Jul. 24, 2020, 10 pages".
"PCT International Search Report and Written Opinion in PCT/US2020/015535 dated May 4, 2020, 13 pages".
"PCT International Search Report and Written Opinion in PCT/US2020/041097 dated Oct. 27, 2020, 18 pages".
"PCT International Search Report and Written Opinion in PCT/US2020/041312 dated Oct. 19, 2020, 11 pages".
"PCT International Search Report and Written Opinion in PCT/US2020/044942 dated Oct. 16, 2020, 15 pages".
"PCT International Search Report and Written Opinion in PCT/US2020/044951 dated Oct. 14, 2020, 14 pages".
"PCT International Search Report and Written Opinion in PCT/US2020/057611 dated Feb. 5, 2021, 11 pages".
"PCT International Search Report and Written Opinion in PCT/US2020/065229 dated Mar. 29, 2021, 11 pages".
"PCT International Search Report and Written Opinion in PCT/US2021/027214 dated Jul. 19, 2021, 14 pages".
"PCT International Search Report and Written Opinion in PCT/US2021/027218 dated Jul. 22, 2021, 14 pages".
"PCT International Search Report and Written Opinion in PCT/US2021/027219 dated Oct. 22, 2021, 22 pages".
"PCT International Search Report and Written Opinion in PCT/US2021/027220 dated Jul. 21, 2021, 15 pages".
"PCT Invitation to Pay Additional Fees in PCT/US2021/019546, mailed on Jun. 15, 2021, 17 pages".
"PCT Invitation to Pay Additional Fees in PCT/US2021/027219, mailed on Jul. 22, 2021, 15 pages".
"Ruhof Dry Sponges", Ruhof, Sep. 30, 2016, https://www.ruhof.com/products/ruhof-dry-sponges (Year: 2016).
Final Office Action in U.S. Appl. No. 17/229,173 dated May 22, 2024, 28 pages.
Non-Final Office Action in U.S. Appl. No. 16/923,238 dated Feb. 28, 2024, 18 pages.
Non-Final Office Action in U.S. Appl. No. 17/992,169 dated May 8, 2024, 13 pages.

\* cited by examiner

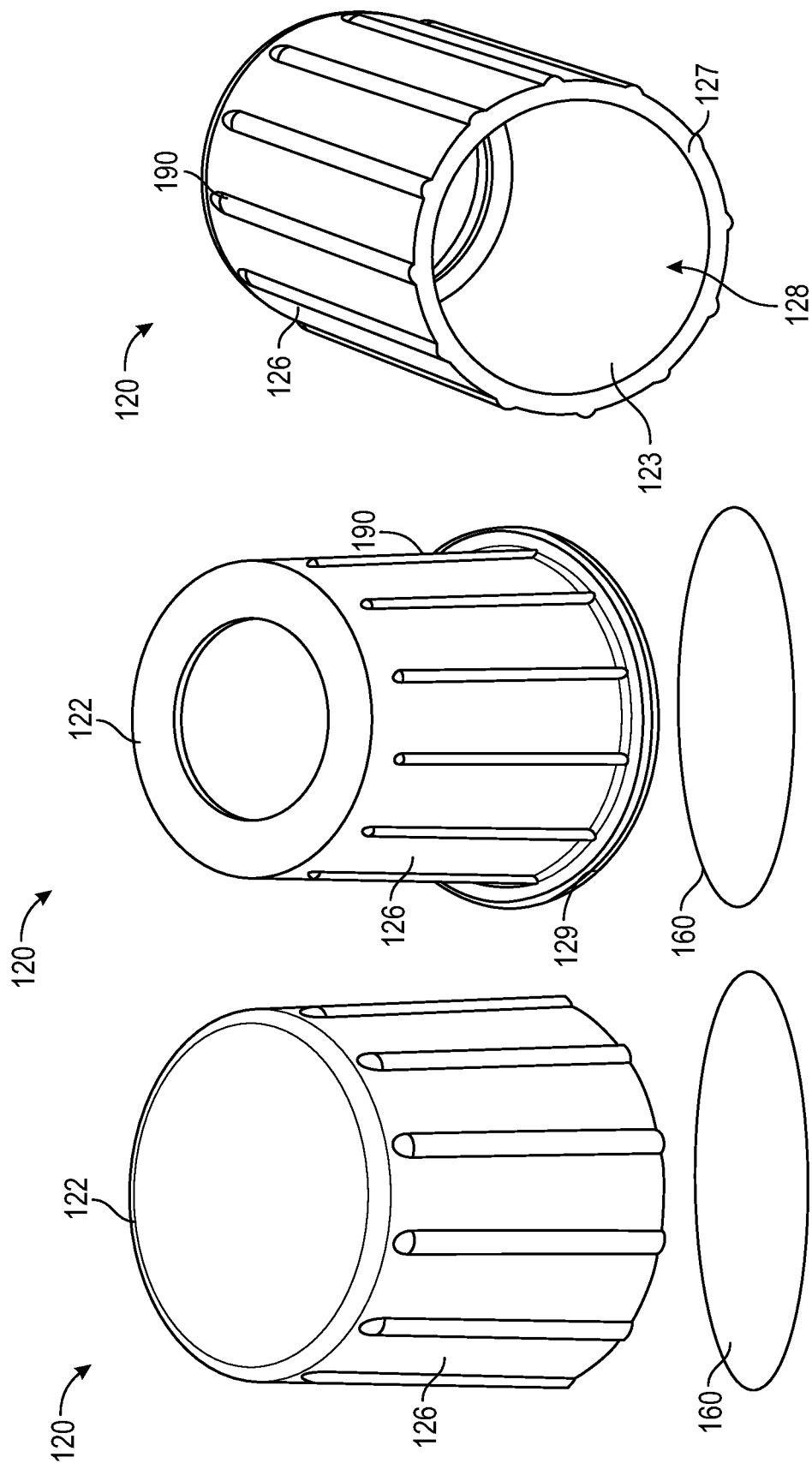

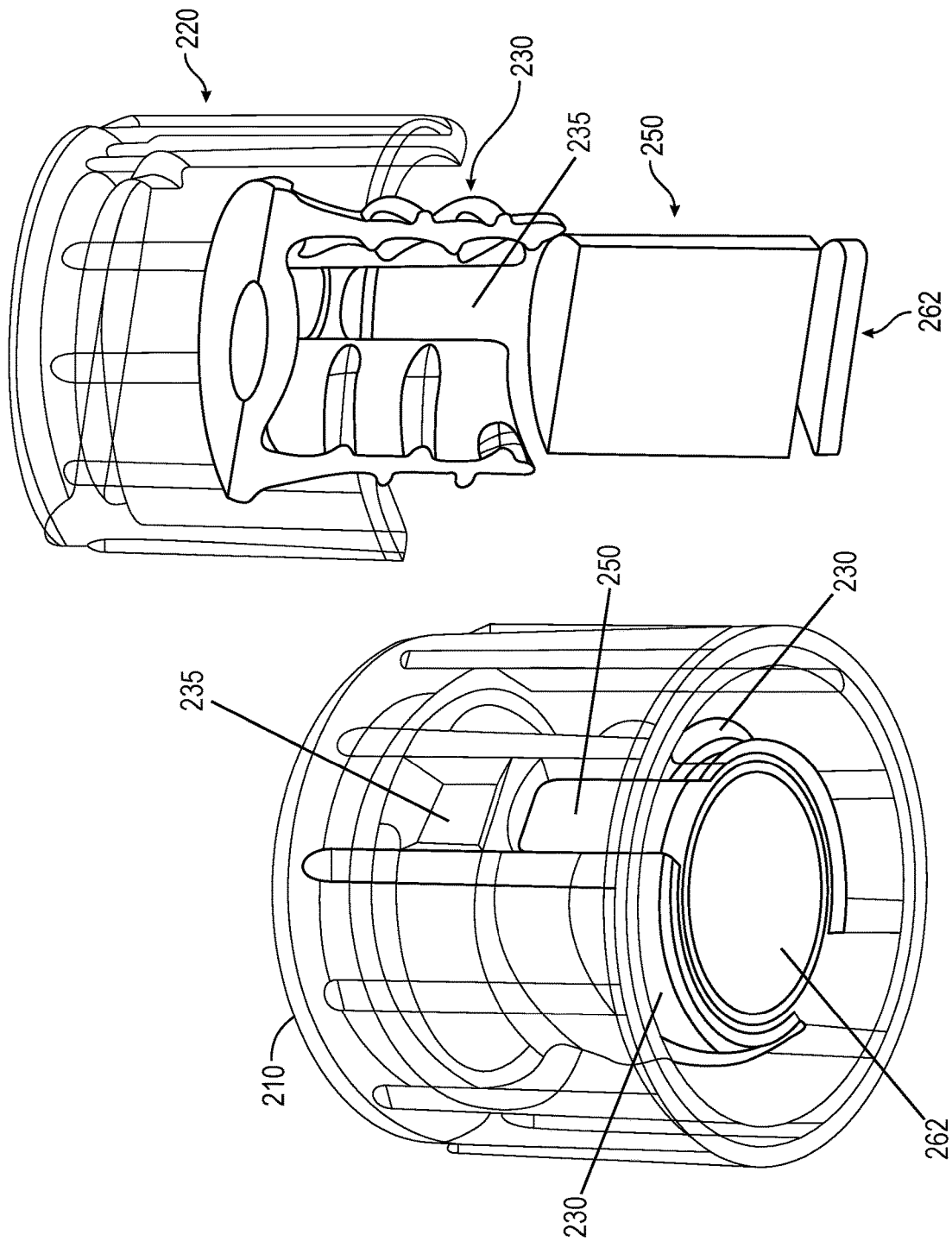

UNIVERSAL CONNECTOR OR CAP FOR MALE AND FEMALE THREADED FITTINGS

CROSS-REFERENCE TO RELATED APPLICATIONS

This application is a continuation of U.S. patent Application Ser. No. 17/076,102, now U.S. Pat. No. 11,353,1147, filed on Oct. 21, 2020, now allowed, which is a continuation of U.S. patent application Ser. No. 16/261,761, filed on Jan. 30, 2019, now issued as U.S. Pat. No. 10,871,246 on Dec. 22, 2020, which claims priority under 35 U.S.C. § 119(e) to U.S. Provisional Application No. 62/623,858, filed Jan. 30, 2018, the disclosures of which are incorporated herein by reference in their entirety.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors. Generally, exemplary embodiments of the present disclosure relate to the fields of threaded fitting, including medical caps and medical disinfection caps, and in particular caps and/or disinfection caps for uses with fluid luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and early indications are that caps will also be incorporated into the 2016 Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are, therefore, limited to the types of connectors to which the cap can be attached. Currently, there are male disinfecting cap devices for disinfecting ISO594-2 type of female threaded fluid luer connectors and there are female disinfecting cap devices for disinfecting ISO594-2 type of male threaded fluid luer connectors. However there is not a singular universal disinfecting cap device with features allowing it to interface with either a male or female type of threaded connectors. Thus, prior disinfecting caps were designed to fit one type of connector only, and were specific to one particular size and/or shape of connector. Thus, there is a need for a disinfecting device capable of accommodating multiple types of connectors, including both male and female connectors, to streamline the disinfecting process.

In the example of medical applications, various conventional caps for closing off a needleless connector while not in use have been known for some time. In order to decrease Catheter-related bloodstream infection (CRBSI) cases disinfection caps were originally disclosed in U.S. Patent Publication No. 2007/011233 which issued as U.S. Pat. No. 8,740,864 (the entire disclosures of both of which are incorporated herein by reference), and introduced on the market. Disinfection caps such as those disclosed in the U.S. Pat. No. 8,740,864 are illustrated in FIGS. 1 and 2 herein, where cap 1 includes a disinfecting pad 2 and a lid 3, and cap 4 includes a disinfecting pad 5 and lid 7, as well as, threads 6 on its inner circumference 8 to interlock with needleless connector hub. On the other hand, other conventional caps may have similar features but exclude the disinfecting pad.

SUMMARY

A first aspect of the present disclosure relates to a cap including a housing and a protrusion. The housing can include a top wall, an essentially cylindrical sidewall forming a first cavity, and an open bottom formed by the cylindrical sidewall with an opening to the first cavity within the housing for receiving a hub of a female needleless connector or a male needleless connector. In one embodiment, the protrusion is integrally formed with the housing and positioned within the first cavity. The protrusion includes an inner surface and an outer surface, the inner surface of the protrusion defining a second cavity. An inner thread can be included on the inner surface of the protrusion, the inner thread being sufficient to interlock with a mating feature of the female needleless connector. An outer thread can be included on the outer surface of the protrusion, the outer thread being sufficient to interlock with a mating feature of the male needleless connector. In one or more embodiments, the protrusion can include one or more cantilevered prongs separated by one or more respective gaps. In one or more embodiments, at least one of the prongs can be configured to bend to facilitate interference fit between the protrusion and the mating feature of the male needleless connector or female needleless connector. In one or more embodiments, the protrusion can extend essentially from an inner surface of the top wall toward the open bottom of the housing. In one or more embodiments, the protrusion can extend essentially parallel to the sidewall of the housing.

A second aspect of the present disclosure relates to a cap including a housing and a removable insert. The housing can include a top wall, an essentially cylindrical sidewall forming a first cavity, and an open bottom formed by the cylindrical sidewall with an opening to the first cavity within the housing for receiving a hub of a female needleless connector or a male needleless connector. The removable insert can be positioned within the first cavity. The removable insert can include a closed distal end comprising a distal wall, an open proximal end, a sidewall extending proximally from the distal wall toward the open proximal end. The sidewall can include a split-thread protrusion integrally formed with the distal wall, the split-thread protrusion having an inner surface and an outer surface. The inner surface of the split-thread protrusion defines a second cavity.

An inner thread can be included on the inner surface of the split-thread protrusion, the inner thread being sufficient to interlock with a mating feature of the female needleless connector. An outer thread can be included on the outer surface of the split-thread protrusion, the outer thread being sufficient to interlock with a mating feature of the male needleless connector.

In one or more embodiments, the split-thread protrusion can include one or more cantilevered prongs separated by one or more respective gaps, in which at least one of the prongs configure to bend to facilitate interference fit between the protrusion and the mating feature of the male needleless connector or female needleless connector. In one or more embodiments, the cap further includes one or more bridge sections arranged to span between the one or more gaps of the one or more cantilevered prongs of the split-thread protrusion.

The sidewall of the removable insert comprises an upper portion and a lower portion. In one or more embodiments, the upper portion of the sidewall can tapered outward toward the distal wall and the lower portion of the sidewall can be cylindrical.

A third aspect of the present disclosure relates to a cap including a housing, a removable insert, an absorbent material, a disinfectant or an antimicrobial agent and a septum. In one or more embodiments, the housing comprises a top wall, an essentially cylindrical sidewall forming a first cavity, and an open bottom formed by the cylindrical sidewall with an opening to the first cavity within the housing for receiving a hub of a female needleless connector or a male needleless connector. In one or more embodiments, the removable insert can be positioned within the first cavity. In one or more embodiments, the removable insert comprises a closed distal end comprising a distal wall, an open proximal end, a sidewall extending proximally from the distal wall toward the open proximal end. In one or more embodiments, the sidewall comprises a split-thread protrusion integrally formed with the distal wall, the split-thread protrusion having an inner surface and an outer surface. In one or more embodiments, the inner surface of the split-thread protrusion defines a second cavity. In one or more embodiments, an inner thread can be disposed on the inner surface of the split-thread protrusion, the inner thread being sufficient to interlock with a mating feature of the female needleless connector. In one or more embodiments, an outer thread is disposed on the outer surface of the split-thread protrusion, the outer thread being sufficient to interlock with a mating feature of the male needleless connector. In one or more embodiments, the absorbent material can be configured within the second cavity. In one or more embodiments, the disinfectant or antimicrobial agent disinfects an outer surface and an inner surface of the female needleless connector or male needleless connector when the female needleless connector or male needleless connector is inserted into the second cavity. In one or more embodiments, the septum can be attached to the open bottom of the insert thereby forming a seal for maintaining the disinfectant or an antimicrobial agent within the second cavity prior to use of the cap. In one or more embodiments, an exterior wall surface of the sidewall of the housing can include a plurality of grip members.

In one or more embodiments, the split-thread protrusion comprises one or more cantilevered prongs separated by one or more respective gaps. In one or more embodiments, at least one of the prongs configure to bend to facilitate interference fit between the protrusion and the mating feature of the male needleless connector or female needleless connector.

In one or more embodiments, the cap further includes one or more bridge sections arranged to span between the gaps of the one or more cantilevered prongs of the split-thread protrusion.

In one or more embodiments, the sidewall of the insert comprises an upper portion and a lower portion. In one or more embodiments, the upper portion of the sidewall can be tapered outward toward the distal wall and the lower portion of the sidewall can be cylindrical.

In one or more embodiments, when a hub of the female needleless connector is received within the inner surface of the second cavity, the hub is secured within the inner surface of the second cavity by interlocking at least a portion of the inner thread with a mating feature on the hub of the female needleless connector. In one or more embodiments, when a hub of the male needleless connector is received within the inner surface of the second cavity, the hub is secured within the first cavity by interlocking at least a portion of the outer thread on the outer surface of the protrusion with a mating feature on a collar of the male needleless connector when the collar is received within an outer portion of the second cavity.

In one or more embodiments, an inner portion of the second cavity can extend further into the housing toward the top wall than an outer portion of the second cavity. In one or more embodiments, the profile of the inner thread can be essentially parallel to, or coincide with, a profile of the outer thread.

In one or more embodiments, the inner thread and outer thread can include an inclined thread pattern. In one or more embodiments, the inner thread and outer thread can include a helical-shaped thread pattern. In one or more embodiments, the inner thread or the outer thread can include one or more gaps in the thread pattern.

In one or more embodiments, the inner surface of the protrusion can be essentially parallel to the outer surface of the protrusion.

In one or more embodiments, at least one absorbent material is configured within the second cavity. In one or more embodiments, the cap can include a removable peel seal the opening to the second cavity to seal the absorbent material within the second cavity prior to use of the cap. In one or more embodiments, the absorbent material can be a foam or a sponge. In one embodiment, the foam can be a polyurethane foam. In one or more embodiments, the absorbent material can include slits. In one or more embodiments, a compression of the absorbent material toward the top wall of the housing occurs upon connection to the female needleless connector, whereby compression of the absorbent material disinfects the female needleless connector. In one or more embodiments, the absorbent material can be under radial compression by the inner thread on the inner surface of the split-thread protrusion to retain the absorbent material in the second cavity.

In one or more embodiments, the disinfectant or the antimicrobial agent can be selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In one or more specific embodiments, the disinfectant or antimicrobial agent includes at least one of chlorhexidine gluconate and chlorhexidine diacetate.

A fourth aspect of the present disclosure pertains to a method of disinfecting a medical connector. The method comprises connecting the cap of one or more embodiments to a medical connector, wherein connecting includes engaging the threads of the medical connector onto the threads on the inner or outer surface of the second cavity of the cap upon insertion of the medical connector into the cap such that the medical connector contacts the absorbent material and the disinfectant or antimicrobial agent.

A fifth aspect of the present disclosure pertains to an assembly. The assembly comprises the cap of one or more embodiments connected to a medical connector. In one or more embodiments, the medical connector is selected from a male luer connector, a female luer connector, and needleless connector.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

FIG. 12 illustrates a perspective top view of an exemplary housing according to one or more embodiments of a second aspect of the disclosure;

FIG. 13 illustrates a perspective top view of an exemplary housing according to one or more alternate embodiments of a second aspect of the disclosure;

FIG. 14 illustrates a perspective bottom view of an exemplary housing according to one or more embodiments of a second aspect of the disclosure;

FIG. 43A illustrates a perspective view of an exemplary cap according to one or more embodiments of a third aspect of the disclosure;

FIG. 43B illustrates a exploded cross-sectional view of an exemplary cap according to one or more embodiments of a third aspect of the disclosure;

DETAILED DESCRIPTION

Figure 1:
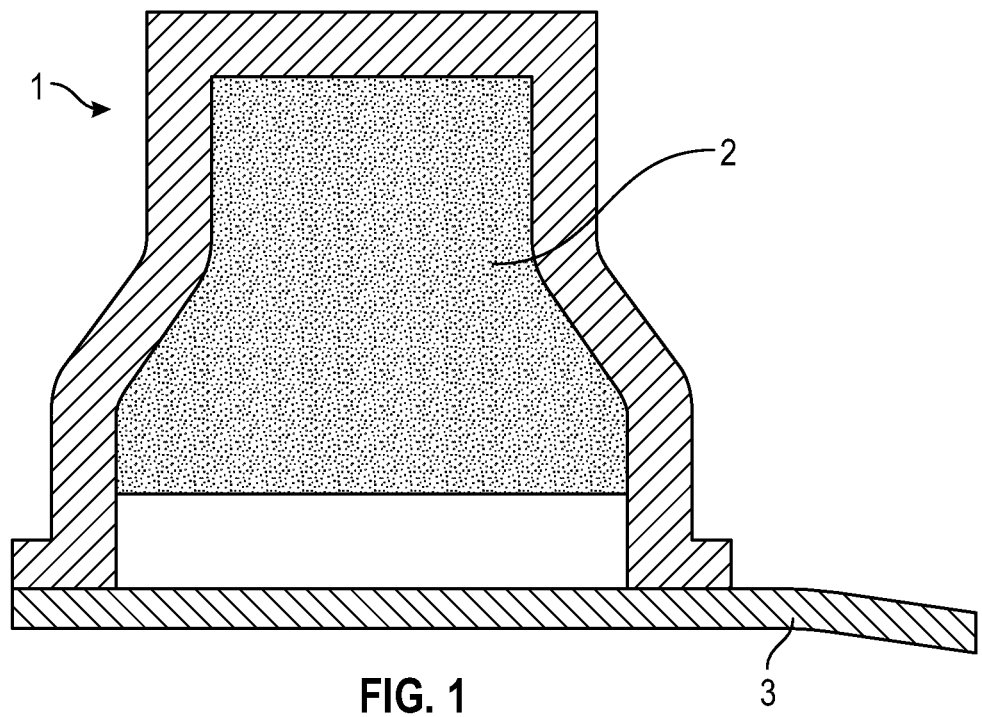
FIGS. 1 and 2 illustrate exemplary prior art.
Figure 2:
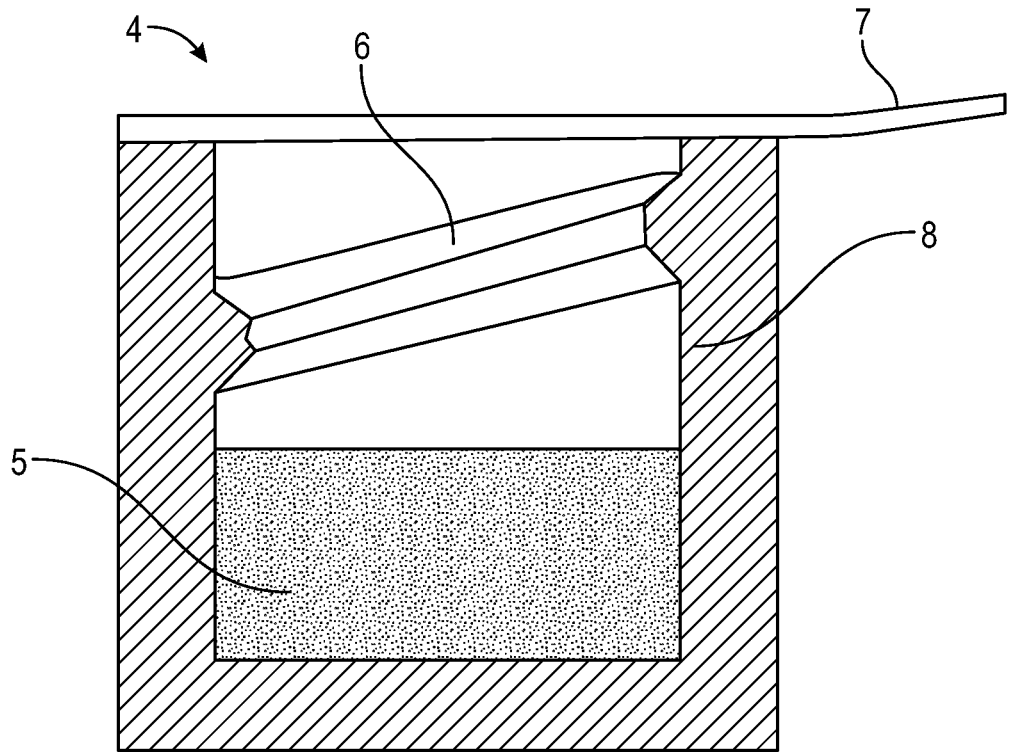
Figure 3A:
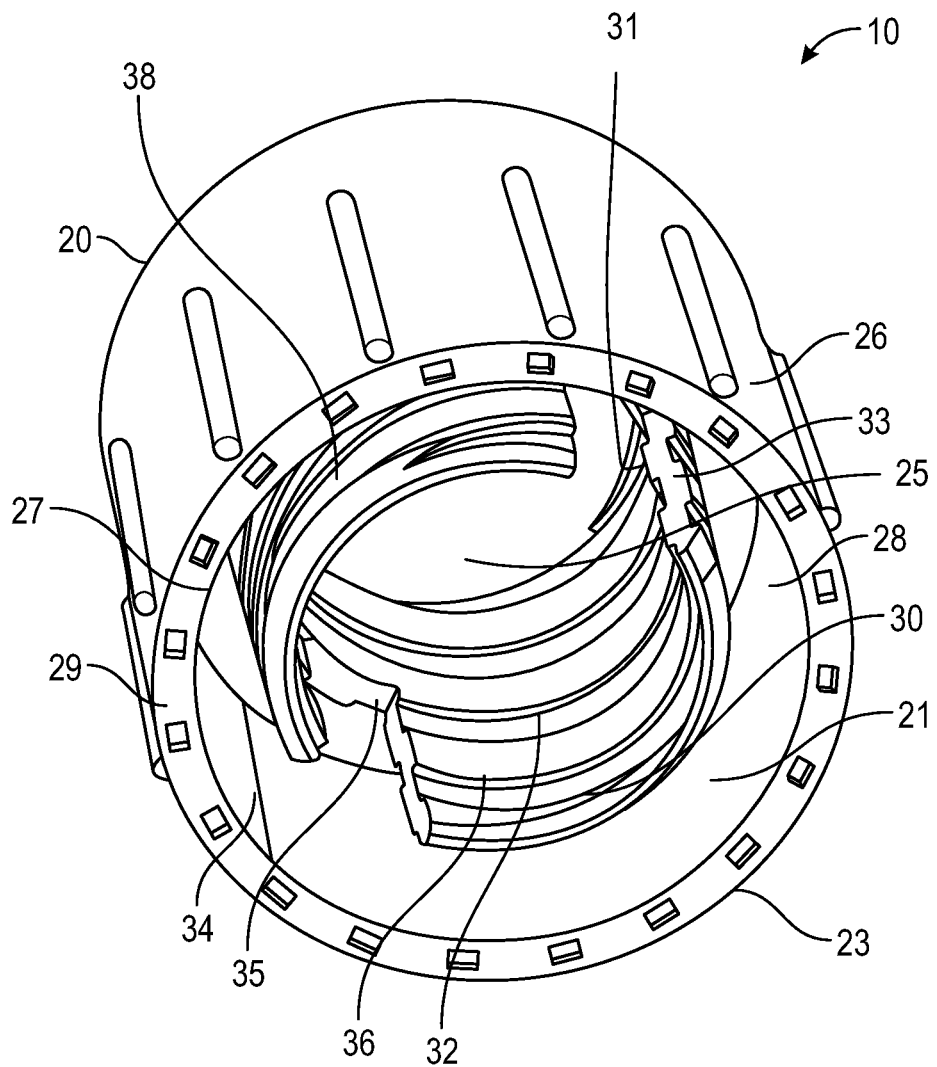
FIGS. 3A and 3B illustrate perspective bottom and top views of a cap according to exemplary embodiments of the disclosure.
Figure 3B:
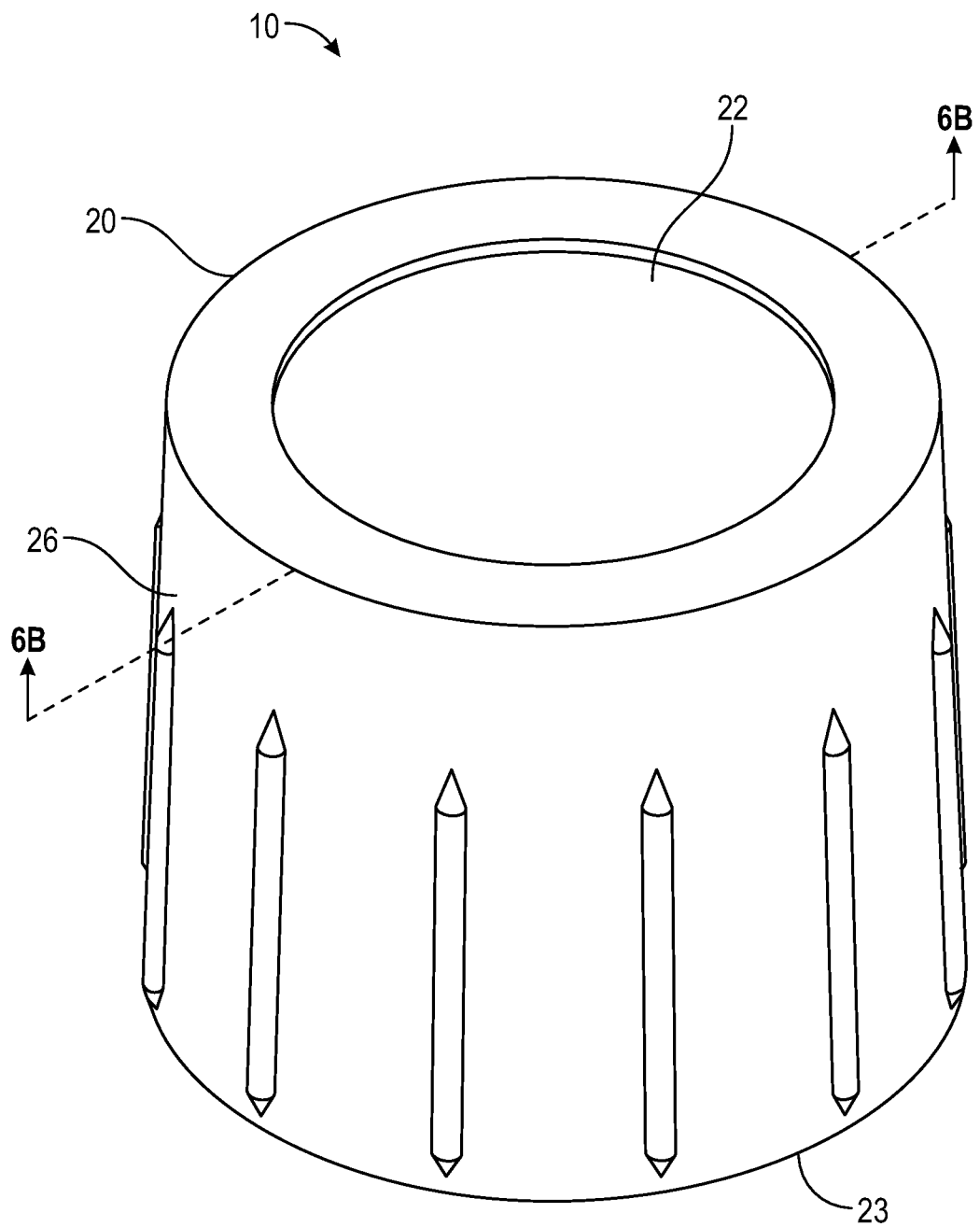

Embodiments of the disclosure pertain to a sterile, universal cap for connection to and disinfection of a medical connector, including male connectors and female connectors. The male connectors and female connectors can be male luer connectors and female luer connectors. Embodiments of the cap comprise a housing and a protrusion. The cap comprises an integral body having a closed end and an open end. The sidewall of the housing having a length $L_C$ extending from the closed end to an open end and defining a chamber. In one or more embodiments, the open end includes a peripheral ledge extending radially outward from the open end defining an end face and an engagement surface. The protrusion having an interior wall surface having one or more threads adapted to engage a female luer connector. The exterior wall surface of the protrusion having one or more threads that are sized and adapted to receive a male luer connector. The cap may further comprise absorbent material, a disinfectant or the antimicrobial agent and a peelable seal and/or septum. The cap provides a mechanical barrier for connectors and contains an antimicrobial agent for disinfection. The cap of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "hole", "tip", "hub", "thread", "sponge", "prong", "protrusion", "tab", "slope", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Exemplary embodiments of the present disclosure provide caps that can reduce the number of device types and logistics currently needed in the hospital setting for connecting, capping, and/or disinfecting male and female threaded fluid luer connectors, by roughly half by including in a single cap or device features allowing it to be use with both male and female threaded fittings.

In an exemplary implementation of the embodiments of present disclosure, a cap, connector cap or disinfecting cap includes integrated thread, or threads, and other features in any and all combinations allowing it to interface with both male and female threaded fittings.

According to further exemplary implementations of the embodiments of the present disclosure, configuration of structural elements making up the cap include one or more cantilevered prongs disposed in cap's inner cavity, the cantilevered prongs comprising an inner thread to connect to female medical connectors and an outer thread to connect to male medical connectors, to facilitate securing of the cap onto a female fitting or onto a male fitting, respectively.

According to yet further exemplary implementations of the embodiments of the present disclosure, both of the male and female threads coincide with each other on the inner and outer face of the threaded protrusion.

According to still further exemplary implementations of the embodiments of the present disclosure, the cantilevered prong may be in the form of protrusion and may be of a split thread type in which the protrusion may bend in order to allow better interference fit compliance with the fittings.

According to still further exemplary implementations of the embodiments of the present disclosure, female threads are sized and have a thread pattern that will engage with a standard ISO594-2 type of male fitting and/or a male threads that are sized and have a thread pattern that will engage with a standard ISO594-2 type of female fitting. An example of an ISO594-2 type of fitting is a Q-style fitting.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

A first aspect of the present disclosure relates to a cap 10 including a housing and a prong in the form of a protrusion. As shown in FIG. 3A through FIG. 7B, housing 20 can include a top wall 22, an essentially cylindrical sidewall 26 forming a first cavity 28, and an open bottom 23 formed by the cylindrical sidewall 26 with an opening 27 to the first cavity 28 within the housing 20 for receiving a hub of a female needleless connector or a male needleless connector. In one embodiment, protrusion 30 is integrally formed with the housing 20 and is positioned within the first cavity 28. Protrusion 30 includes an inner surface 31 and an outer surface 33, the inner surface 31 of protrusion 30 defining a second cavity 40. In one or more embodiments, the cap 10 of the present disclosure has inner thread 36 that have a size and pitch to engage a threadable segment of a female connector, such as for example, a female luer connector. Such connectors are generally and commonly used as catheter and other fluid-tight protective connectors in medical applications. In some embodiments, cap 10 provides a protective cover for a female luer connector when engaged with the connector when threads from the female luer connector engage and form a releasable connection with inner threads 36 of cap 10. An inner thread 36 can be included on the inner surface 31 of protrusion 30, the inner thread 36 being sufficient to interlock with a mating feature of the female needleless connector. An outer thread 38 can be included on the outer surface 33 of protrusion 30, the outer thread 33 being sufficient to interlock with a mating feature of the male needleless connector. In one or more embodiments, the protrusion 30 can include one or more cantilevered prongs separated by one or more respective gaps. In one or more embodiments, at least one of the prongs can be configured to bend to facilitate interference fit between the protrusion and the mating feature of the male needleless connector or female needleless connector. In one or more embodiments, protrusion 30 can extend essentially from an inner surface of the top wall 22 toward the open bottom 23 of the housing 20. In one or more embodiments, the protrusion 30 can extend essentially parallel to the sidewall of the housing.

Referring to FIGS. 3A through 6B, according to exemplary embodiments of the present disclosure a cap 10 comprises a housing 20 which includes a top wall 22 with an inner surface 25, a sidewall 26 (which can be essentially cylindrical) with an inner surface 21, and an opening 27 into a first cavity 28. Opening 27 is disposed at bottom 23 of housing 20. Inner surface 25 of top wall 22 can form a top of cavity 28. Disposed within cavity 28 is a protrusion 30 (which can be essentially cylindrical and coaxial with sidewall 26) having an inner surface 31 defining an inner portion 32 of cavity 28, and an outer surface 33 defining and outer portion 34 of cavity 28. Protrusion 30 comprises an inner thread 36 on its inner surface 31 for engaging a female connector and an outer thread 38 on its outer surface 33 for engaging a male connector.

In an exemplary implementation, a peel seal 60 can be provided to seal the opening 27 prior to use of cap 10, for example, by attachment to a surface of a rim 29 of an open bottom 23 of housing 20, as described for example in the above-referenced prior applications.

Figure 8:
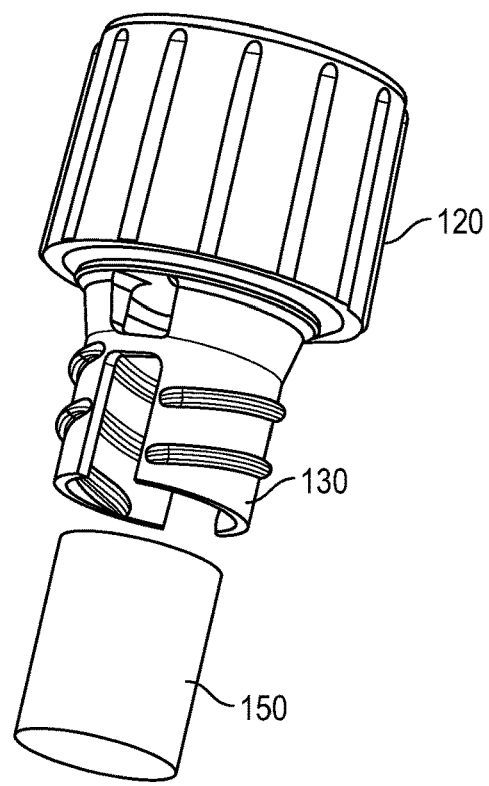
FIG. 8 illustrates a exploded perspective view of an exemplary cap according to one or more embodiments of a second aspect of the disclosure.
Figure 9:
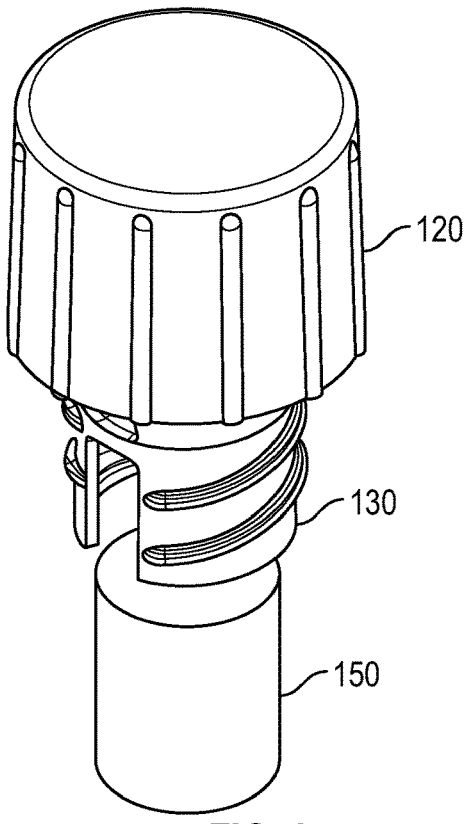
FIG. 9 illustrates a exploded perspective top view of an exemplary cap according to one or more embodiments of a second aspect of the disclosure.
Figure 11:
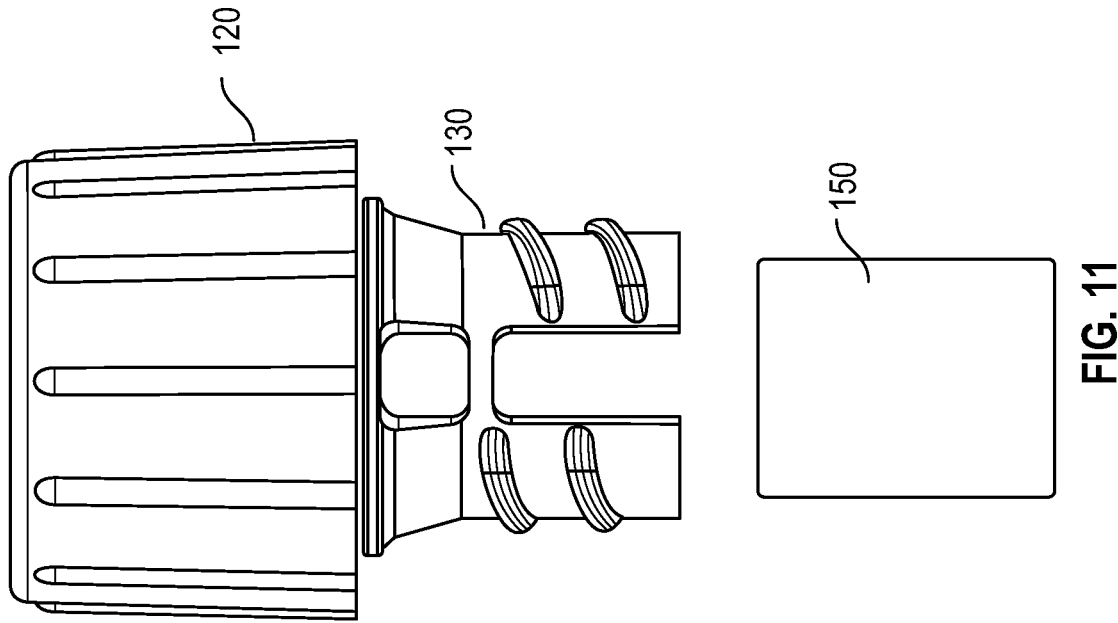
FIG. 11 illustrates a exploded side view of an exemplary cap according to one or more embodiments of a second aspect of the disclosure.
Figure 10:
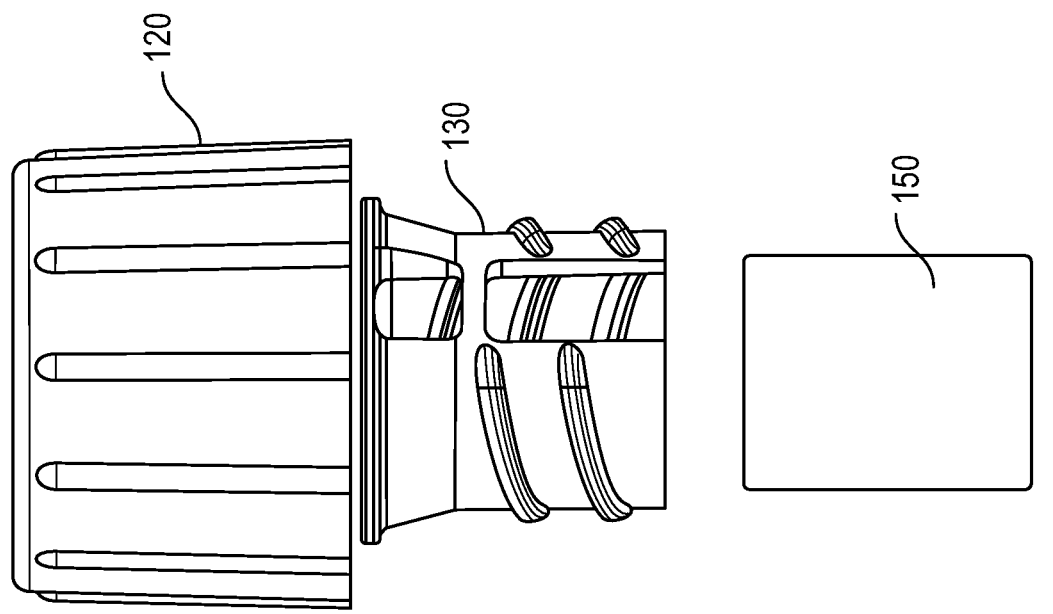
FIG. 10 illustrates a exploded side view of an exemplary cap according to one or more embodiments of a second aspect of the disclosure.
Figure 16:
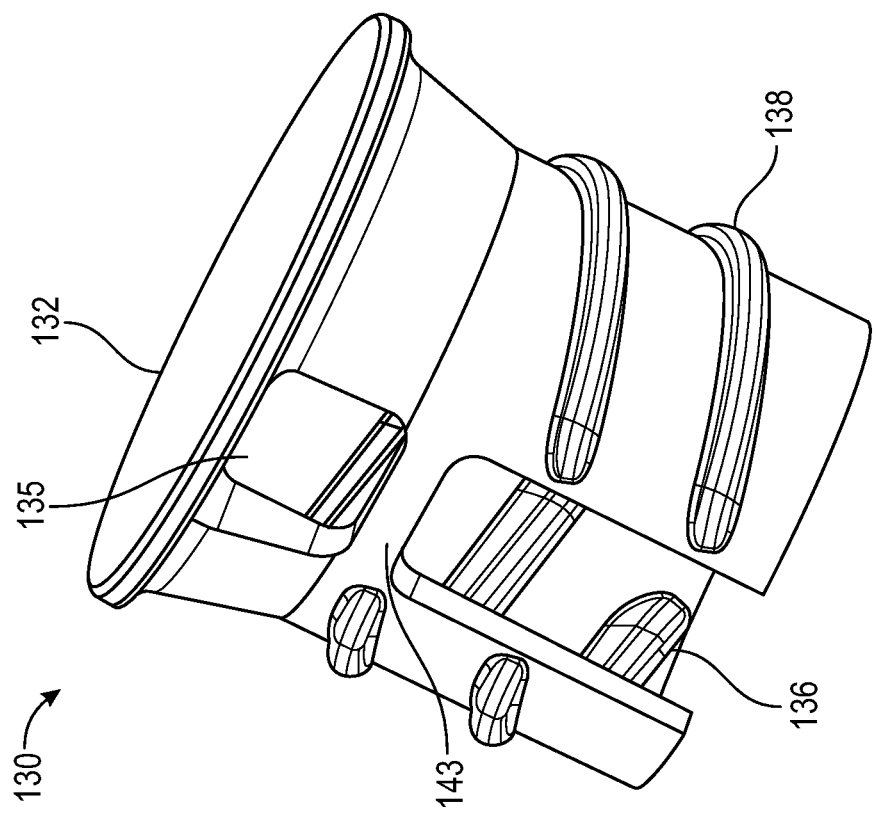
FIG. 16 illustrates a perspective side view of an exemplary removable insert according to one or more embodiments of a second aspect of the disclosure.
Figure 15:
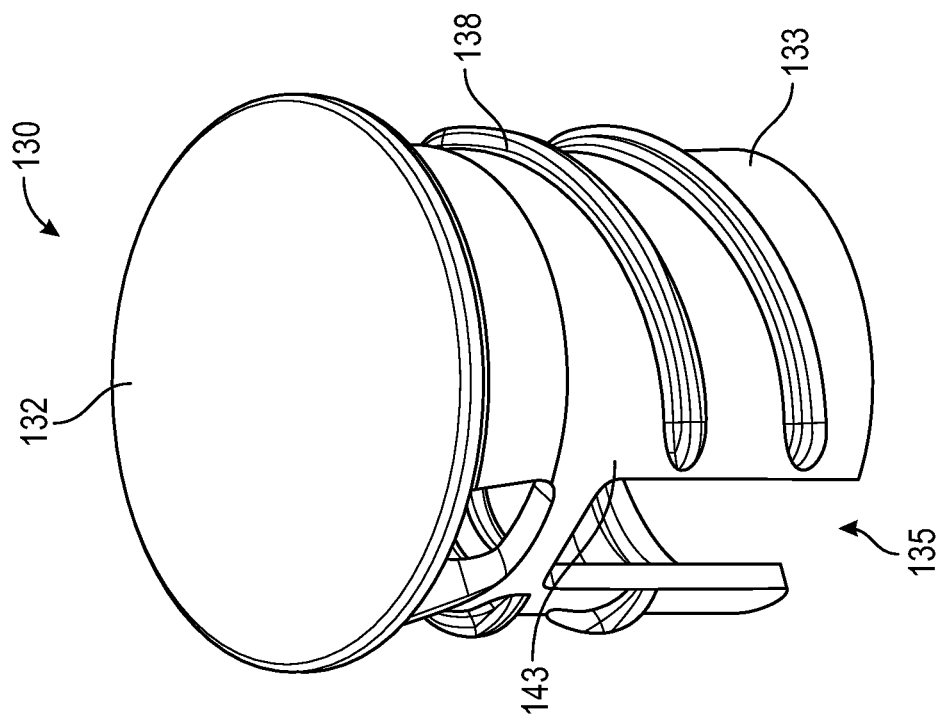
FIG. 15 illustrates a perspective top view of an exemplary removable insert according to one or more embodiments of a second aspect of the disclosure.
Figure 17:
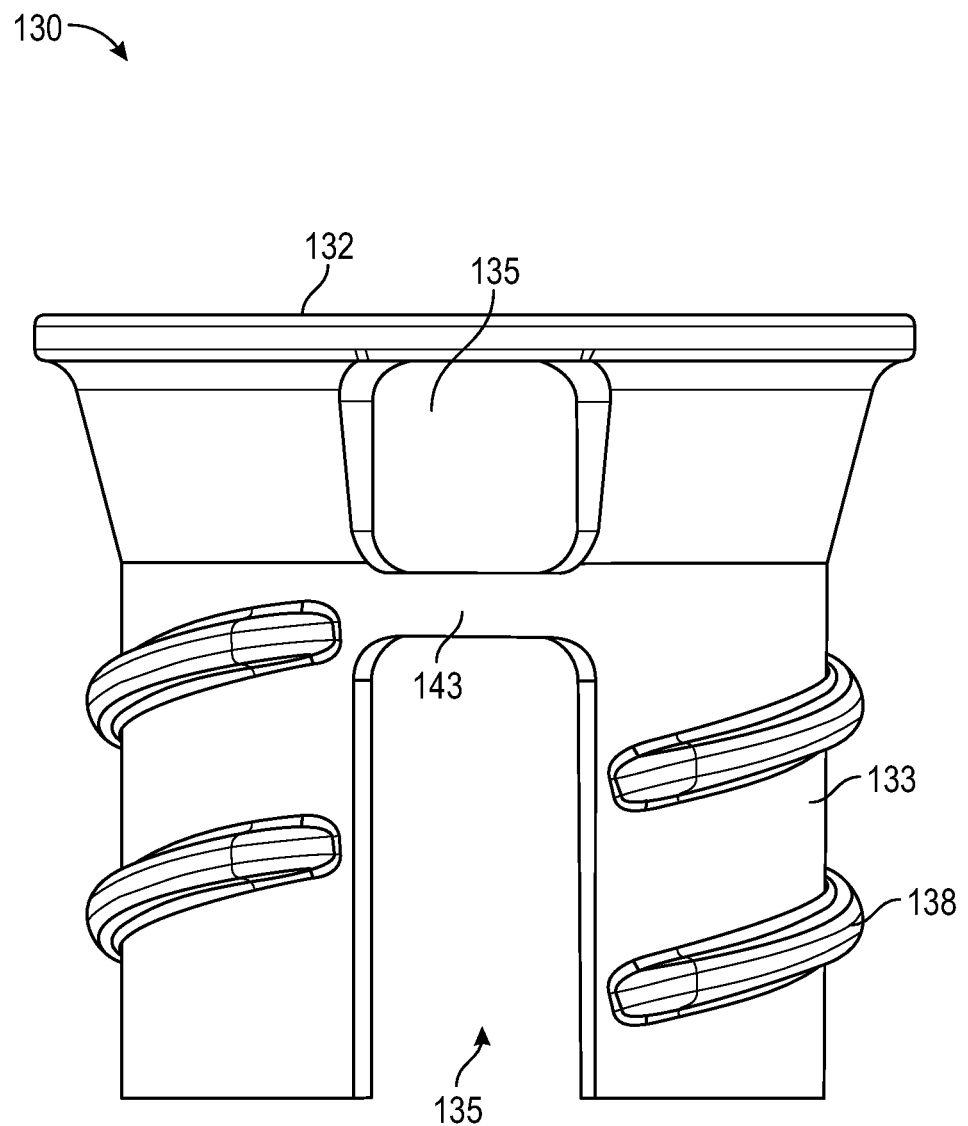
FIG. 17 illustrates a side view of an exemplary removable insert according to one or more embodiments of a second aspect of the disclosure.

Referring to FIG. 8, in one or more embodiments, the peelable seal 60 is disposed on the engagement surface of open bottom 23 of housing 20 to prevent the disinfectant or the antimicrobial agent from exiting the cavity 28. With the absorbent material 50 properly inserted into the cavity 28 of the cap 10, the peelable seal 60 may be secured to the engagement surface of open bottom 23 of housing 20. The peelable seal 60 minimizes entry of potential particulate hazard and also provides a substantially impermeable enclosure for the cap 10, provides a leak prevention and protection enclosure, protects the contents of absorbent material 50 contained within the cavity 28, and/or maintains a sealed, sterilized environment. The peelable seal 60 provides a sufficient seal at a range of temperatures, pressures, and humidity levels.

In one or more embodiments, the peelable seal 60 comprises an aluminum or multi-layer polymer film peel back top. In a specific embodiment, the peelable seal 60 is heat-sealed or induction sealed to the open end of the cap. In one or more embodiments, the peelable seal 60 comprises a moisture barrier.

Figure 4A:
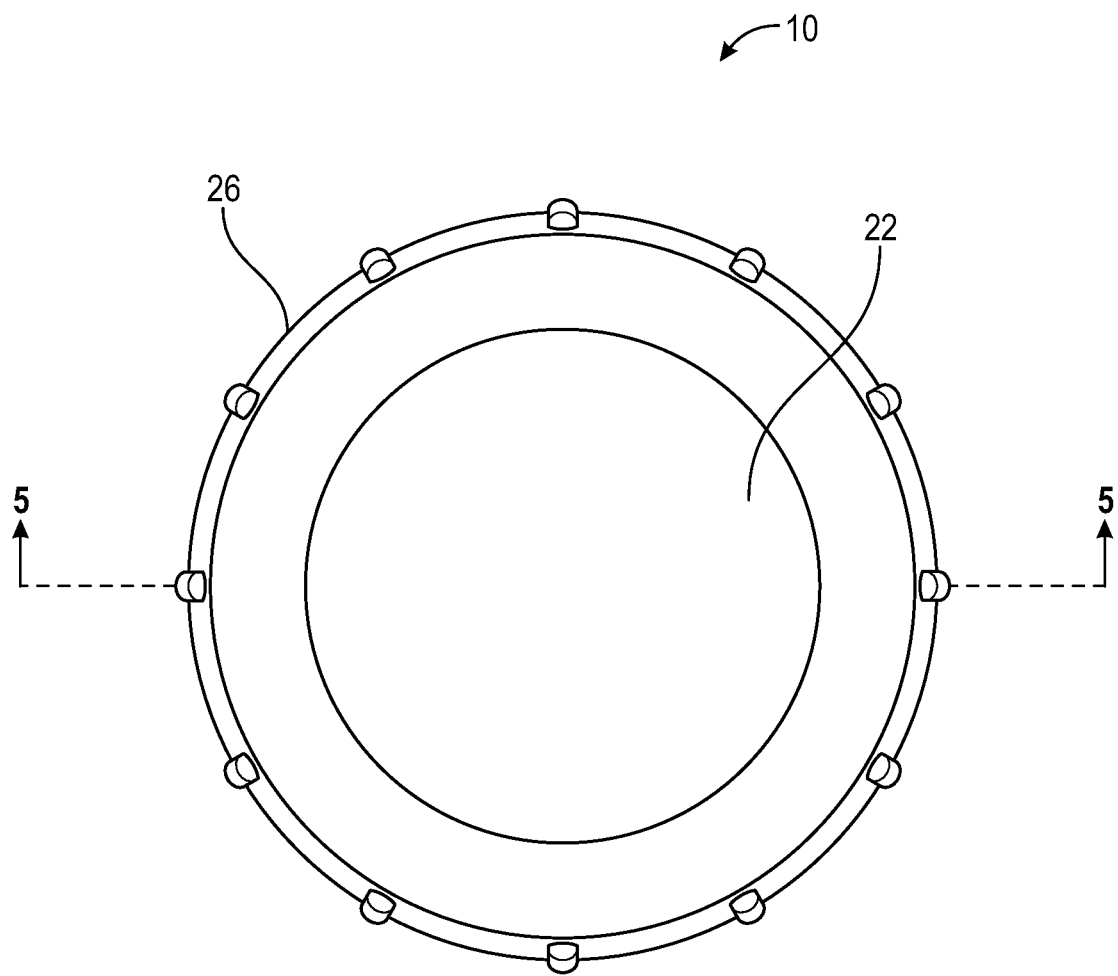
FIGS. 4A, 4B, and 4C illustrate top, side, and bottom views, respectively of a cap shown in FIGS. 3A and 3B.
Figure 4B:
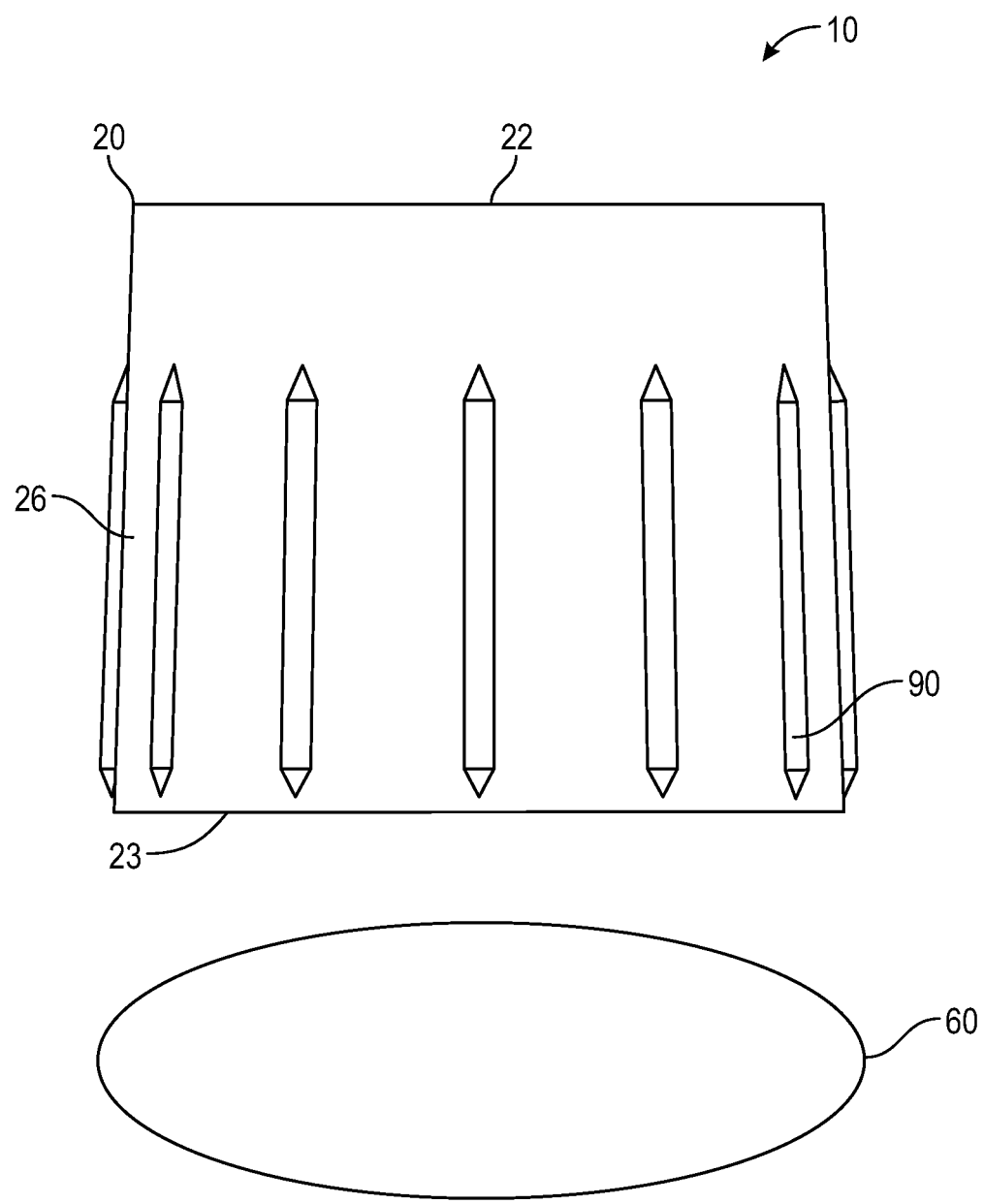
Figure 4C:
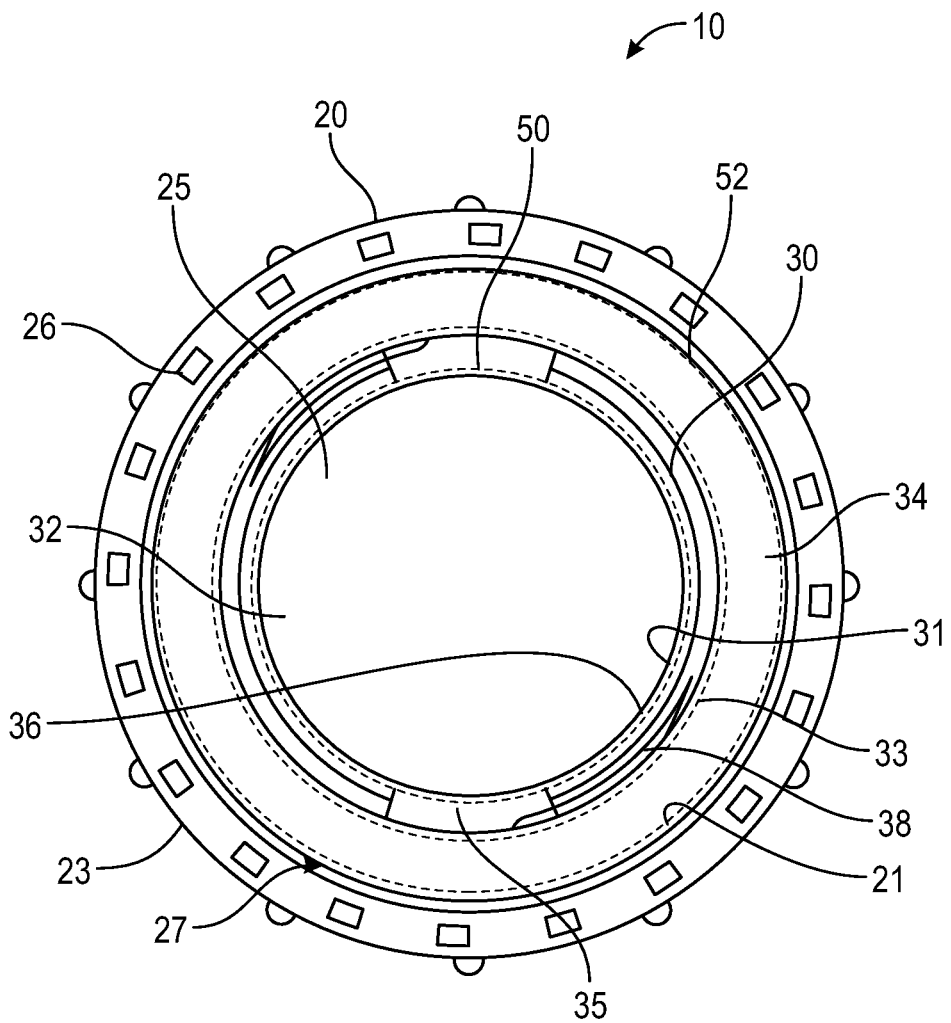
Figure 5:
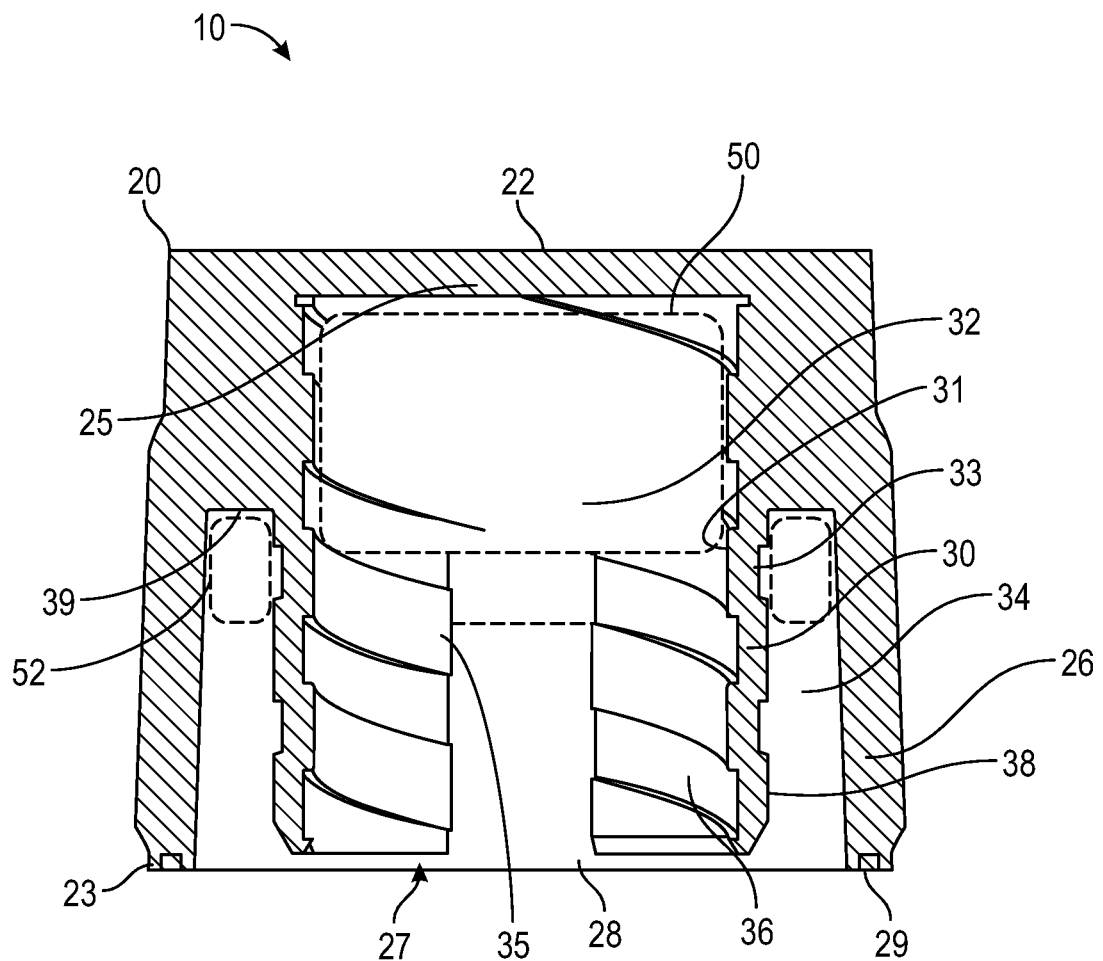
FIG. 5 illustrates a cross sectional views along the line 5-5 of FIG. 4A of a cap shown in FIGS. 3A through 4C.
Figure 6A:
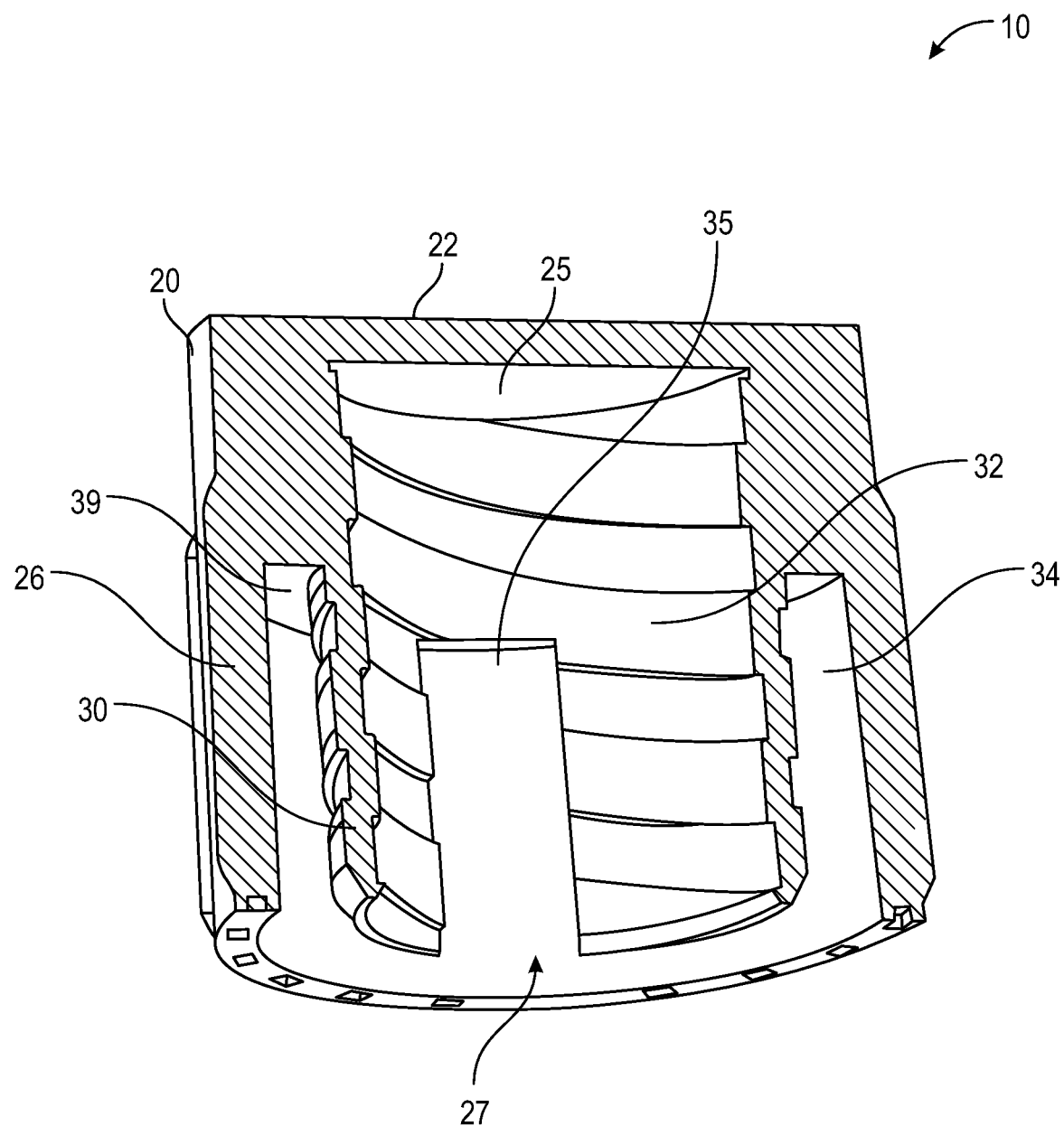
FIGS. 6A and 6B illustrate perspective cross sectional views along the line 6A-6A of FIG. 3A and line 6B-6B of FIG. 3B, respectively, of a cap shown in FIGS. 3A through 5.
Figure 6B:
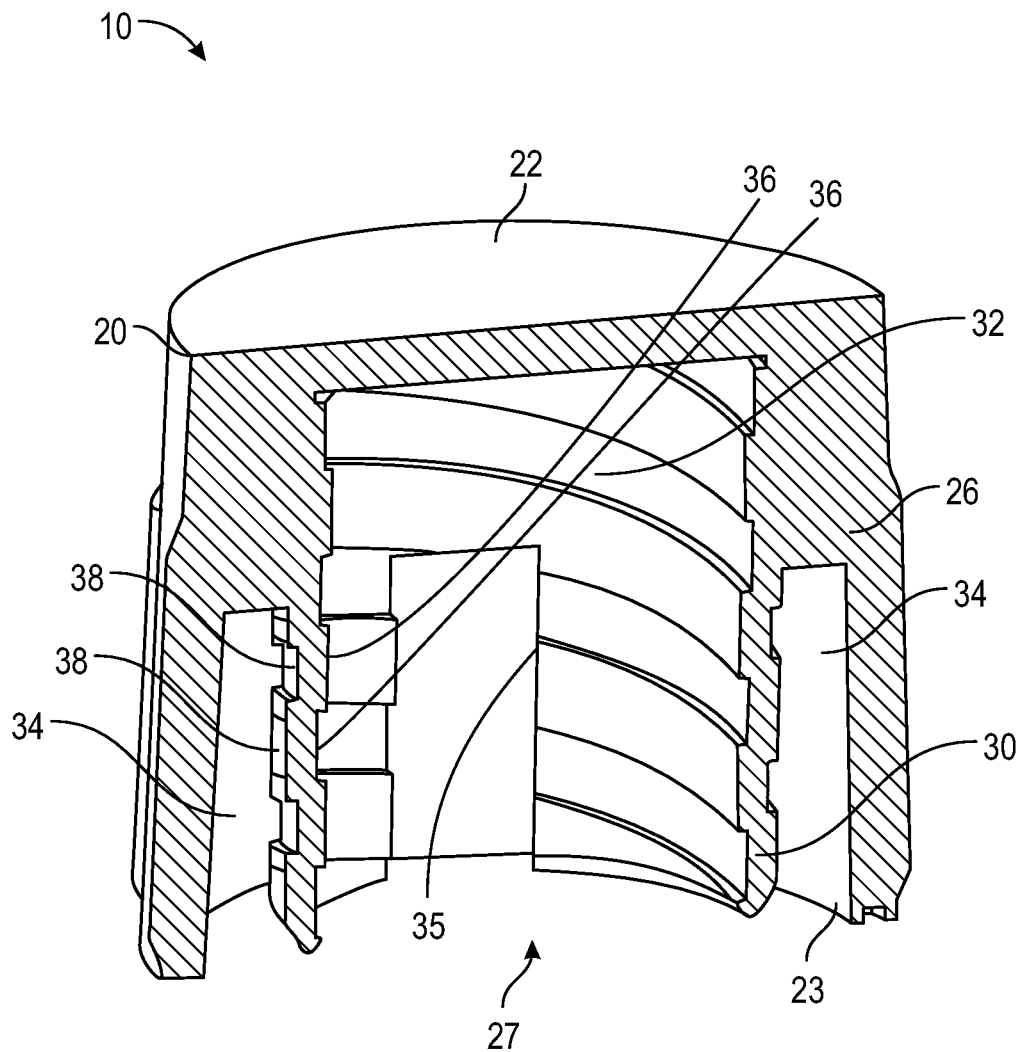

Referring to FIG. 4C, in one or more embodiments, an absorbent material 50 is under radial compression by the inner thread 36 on the inner surface 31 of protrusion 30 to retain the absorbent material 50 in the cavity 28. In one or more embodiments, the absorbent material 50 is a nonwoven material, foam, or a sponge. In a specific embodiment, the foam is a polyurethane foam. In a specific embodiment the absorbent material 50 is in the form of a foam plug. In one or more embodiments, the absorbent material 50 includes one or more slits.

In yet another exemplary implementation, a disinfecting member or members, such as an absorbent material 50, in the form of a IPA soaked sponge and/or sponge. In one or more embodiments, absorbent material 50 can also be formed together as a single cleaning member or separate cleaning member can be provided within cavity 28, for example in the proximity of inner surface 25 of top wall 22 of inner portion 32 and/or towards top 39 of outer portion 34 of cavity 28, for example as described in the above-referenced prior applications.

The cap 10 can achieve disinfection when used on luer connectors by integrating disinfectant or antimicrobial agent in the cavity 28 of the cap 10. The disinfectant or antimicrobial agent can be directly included in the cavity 28 or disinfectant or antimicrobial agent can be absorbed into sponges or foam material that fills the chamber of cap 10. Cap 10 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 50 toward the top wall 22 of housing 20 upon connection to the female luer connector or the male luer connector allows the connector to contact the disinfectant or antimicrobial agent to disinfect the female luer connector or the male luer connector.

In an exemplary implementation of embodiments of the present disclosure, protrusion 30 can be cantilevered, for example by having one or more gaps or cutouts 35. In an exemplary implementation, at least a portion of the a cantilevered protrusion 30 may bend in order to allow better interference fit compliance with the fitting such as at least one of male connector or female connector.

In yet another exemplary implementation, protrusion 30 can extend essentially from inner surface 25 of top wall 22 toward bottom of housing 20.

In still further exemplary implementation, protrusion 30 can extend essentially parallel to sidewall 26.

In yet further exemplary implementation, inner portion 32 of cavity 28 can extend further into the cap toward inner surface 25 of top wall 22 than the outer portion 34 which terminates at top 39, for example as illustrated in the cross section views of FIGS. 5 through 7B.

In still yet further exemplary implementation, a profile of the inner thread 36 and/or the inner surface 31 can essentially parallel, or coincide with, a profile of the outer thread 38 and/or the outer surface 33, respectively.

Figure 7A:
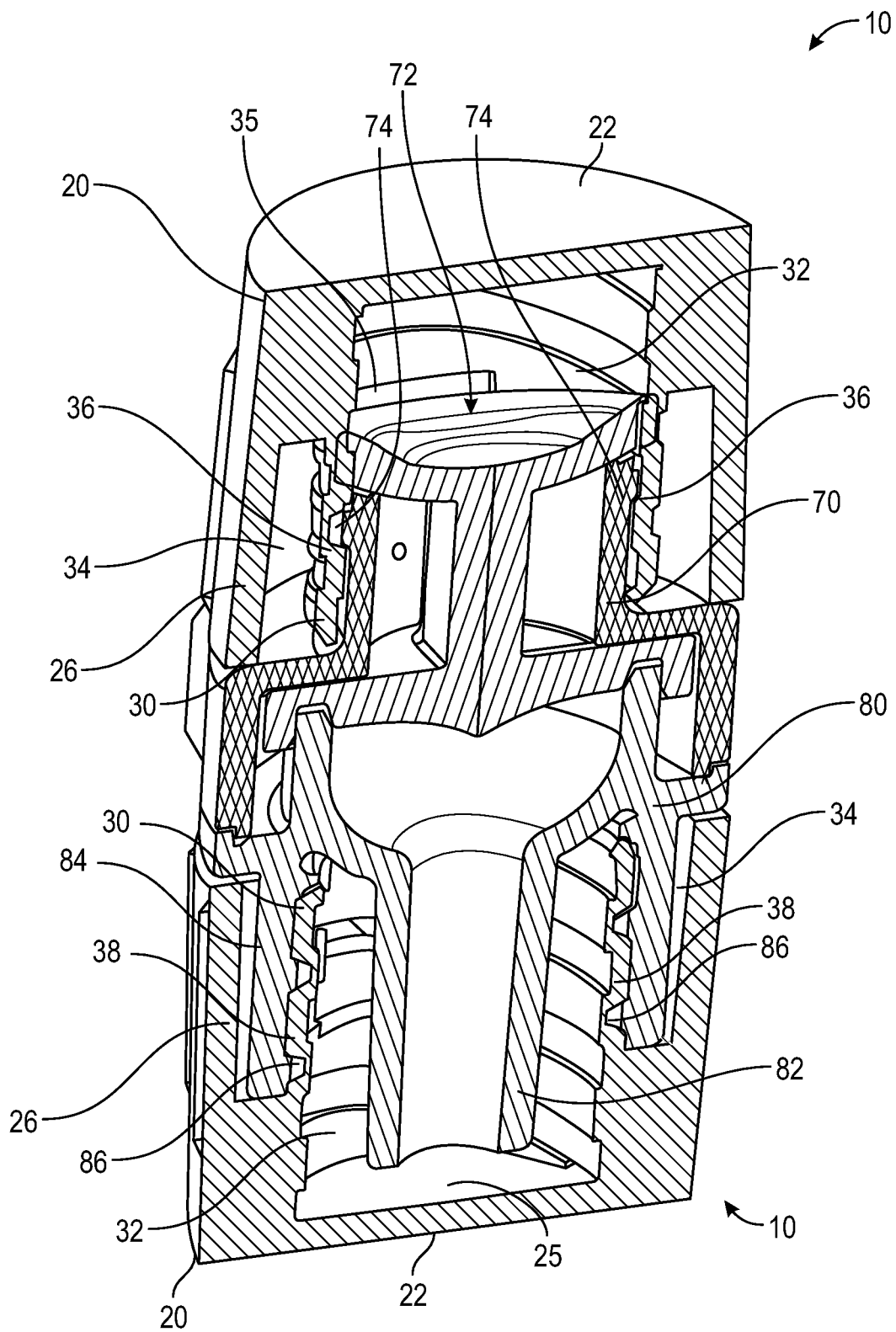
FIGS. 7A and 7B diagrammatically show cross section and perspective cross sectional view of two caps shown in FIGS. 3A though 6B and a typical ISO594-2 type of needleless connector, where one cap is secured onto Q-Syte male connector and the other cap is secured onto the Q-Syte female connector.
Figure 7B:
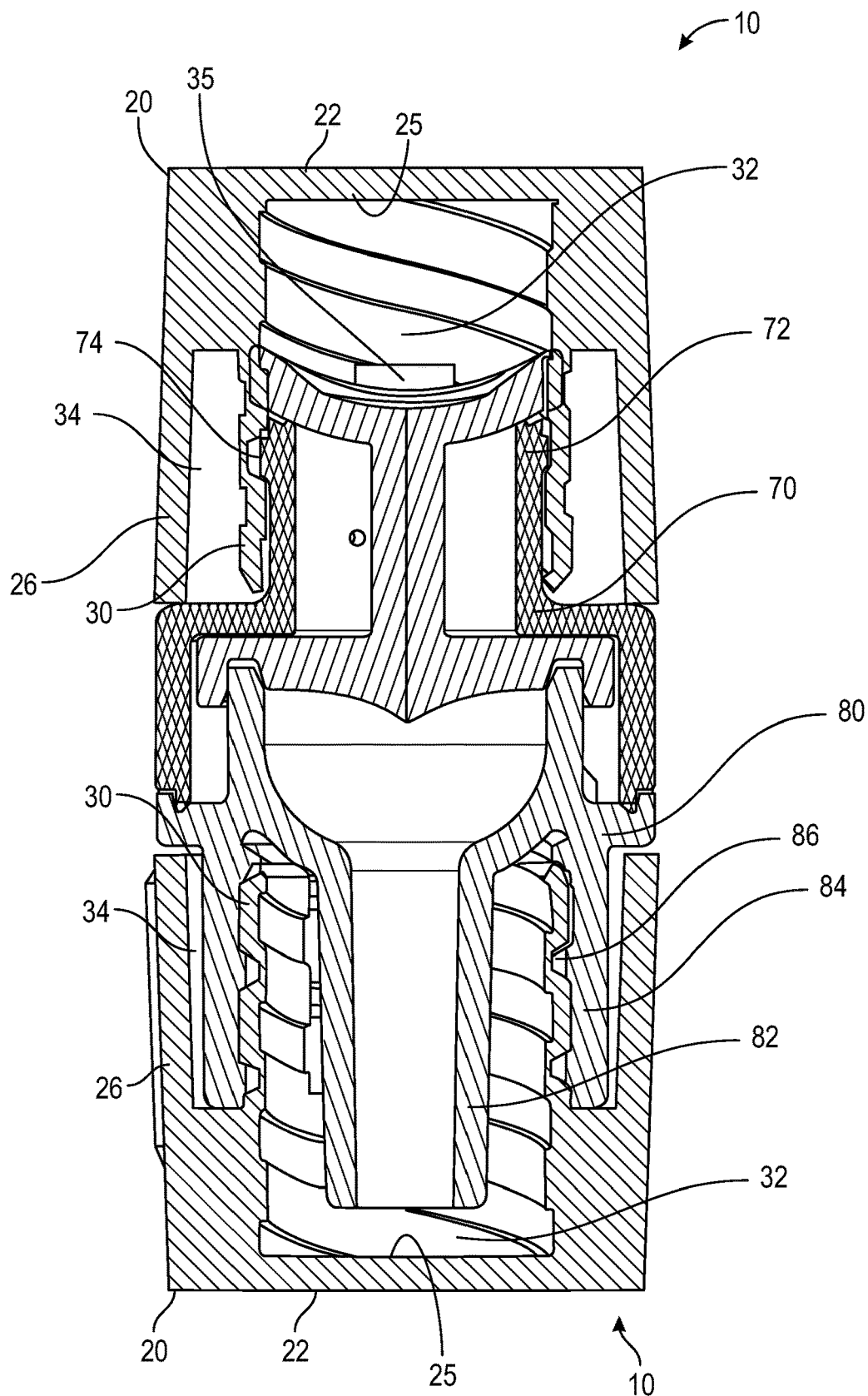

Referring to FIGS. 7A and 7B, according to exemplary embodiments of the disclosure, cap 20 can receive a tip or hub 72 of a female needleless connector 70, for example after a peel seal 60 sealing cavity 28 is removed or when the peal sealing film is pierced, within inner portion 32 of cavity 28 and secure, for example, threadedly, the tip of needleless connector 70 within inner portion 32 of cavity 28. One or more threads 36 can be sufficient to interlock with a mating feature 74 (such as one or more protrusions, lugs and/or thread) of a hub or tip 72 of needleless connector 70, as described for example in related U.S. patent application Ser. Nos. 15/408,278 and 15/408,187, both filed on Jan. 17, 2017.

Referring further to FIGS. 7A and 7B, according to exemplary embodiments of the disclosure, cap 20 can receive a tip or hub 82 of a male needleless connector 80, for example after a peel sealing film sealing cavity 28 is removed or when the peal sealing film is pierced, within inner portion 32 of cavity 28 and secure the tip or hub 82 of needleless connector 80 within the inner portion 32 of cavity 28, by securing, for example, threadedly, collar 84 of connector 80 within outer portion 34 of cavity 28. One or more threads 38 can be sufficient to interlock with a mating feature 86 (such as one or more protrusions, lugs and/or thread) of collar 84 of needleless connector 80.

In an exemplary implementation of FIG. 3A through 7B, protrusion 30 is illustrated as comprising two prongs spaced by cutouts 35 and extending essentially from surface 25 of top wall 22. However, also within the scope of the disclosure are caps comprising a unitary protrusion 30 without any cutouts 35, and caps having protrusion 30 comprising any number of identical and/or different (in any dimensional characteristics, such as length width, thickness, or shape) prongs, as long as protrusion 30 is configure to engage a female connector with respect to its inner surface, and engage a male connector with respect to its outer surface.

Referring to FIGS. 3A-4B, in one or more embodiments, the exterior surface of sidewall 26 comprises a plurality of grip members 90.

The cap 10 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 10 comprises a polypropylene or polyethylene material.

According to exemplary implementations of the embodiments of the disclosure, cap 10 can described above with reference to FIGS. 3A through 7B can further comprise an outer housing implementing the safety features and designs described in U.S. patent applications No. 62/488,266 filed Apr. 21, 2017 and No. 62/523,506, filed Jun. 22, 2017, for example by modifying walls 22 and/or 26 of housing 20.

According to yet further exemplary implementations of the embodiments of the disclosure, cap 10 described above with reference to FIGS. 3A through 7B can be implements with various venting features and designs described in US patent applications Nos. U.S. patent application Ser. Nos. 15/408,278 and 15/408,187, both filed on Jan. 17, 2017, for example by modifying shape and/or size of protrusion 30, and/or configuration (such as pitch, spacing, thickness, and/or other structural features) of thread 36 and/or thread 38, and/or configuration of surface 31 and/or surface 33.

A second aspect of the present disclosure, as shown in FIGS. 8-43, relates to a cap including a housing, and a removable insert and absorbent material. An exploded view of a cap of the second aspect of the present disclosure, as shown in FIGS. 8-11, relates to a cap 110 including a housing 120, and a removable insert 130 and absorbent material 150.

As shown in FIGS. 12-14, housing 120 can include a top wall 122, an essentially cylindrical sidewall 126 (which can be essentially cylindrical) with an inner surface 121 forming a first cavity 128, and an open bottom 123 formed by the cylindrical sidewall 126 with an opening 127 to the first cavity 128 within the housing 120 for receiving a hub of a female needleless connector or a male needleless connector. Opening 127 is disposed at bottom 123 of housing 120. Inner surface 125 of top wall 122 can form a top of cavity 128. Referring to FIGS. 12-14, in one or more embodiments, the exterior surface of sidewall 126 comprises a plurality of grip members 190.

Referring to FIG. 13, rim 129 of an open bottom 123 of housing 120 may comprise a peripheral ledge extending radially outward from the annular sidewall 126. The surface of rim 129 of an open bottom 123 of housing 120 also defines an engagement surface where a peelable seal 160 may be secured.

Referring to FIGS. 12 and 13, in one or more embodiments, the peelable seal 160 is disposed on the engagement surface of open bottom 123 of housing 120 to prevent the disinfectant or the antimicrobial agent from exiting the cavity 128. With the absorbent material 150 properly inserted into the cavity 128 of the cap 110, the peelable seal 160 may be secured to the engagement surface of open bottom 123 of housing 120. The peelable seal 160 minimizes entry of potential particulate hazard and also provides a substantially impermeable enclosure for the cap 110, provides a leak prevention and protection enclosure, protects the contents of absorbent material contained within the cavity 128, and/or maintains a sealed, sterilized environment. The peelable seal 160 provides a sufficient seal at a range of temperatures, pressures, and humidity levels.

In one or more embodiments, the peelable seal 160 comprises an aluminum or multi-layer polymer film peel back top. In a specific embodiment, the peelable seal 160 is heat-sealed or induction sealed to the end face of the locking lid or to the cap open end. In one or more embodiments, the peelable seal 160 comprises a moisture barrier.

As shown in FIGS. 15-19, removable insert 130 can include a closed distal end comprising a distal wall 132 having a lip, an open proximal end 134, a sidewall extending proximally from the distal wall 132 toward the open proximal end 134. The removable insert 130 in the form of a split-thread protrusion having distal wall 132, the split-thread protrusion having an inner surface 131 and an outer surface 133. The inner surface 131 of the split-thread protrusion 130 defines a second cavity 140.

As shown in FIGS. 20-24, an inner thread 136 can be included on the inner surface 131 of the split-thread protrusion 130, the inner thread 136 being sufficient to interlock with a mating feature of the female needleless connector. In one or more embodiments, the cap 110 of the present disclosure has inner thread 136 that have a size and pitch to engage a threadable segment of a female connector, such as for example, a female luer connector. Such connectors are generally and commonly used as catheter and other fluid-tight protective connectors in medical applications. In some embodiments, cap 110 provides a protective cover for a female luer connector when engaged with the connector when threads from the female luer connector engage and form a releasable connection with inner threads 136 of cap 110. In one or more embodiments, the interior wall surface comprises inner threads 136 adjacent to the open end. The inner threads 136 are adapted and sized to engage a female luer connector. In one or more embodiments, the inner threads 136 adjacent the open end of the cap 110 partially extend along a length of the inner surface 131 of split-thread protrusion 130. The inner surface 131 of split-thread protrusion 130 includes one or more gaps 135. The function of the one or more gaps 135 is to accommodate and facilitate engagement with a male luer connector. In one or more embodiments, the thread pattern on the inner surface 131 of split-thread protrusion 130 is inclined. In one or more embodiments, the thread pattern on the inner surface 131 of split-thread protrusion 130 is helical.

An outer thread 138 can be included on the outer surface 138 of the split-thread protrusion 130, the outer thread 138 being sufficient to interlock with a mating feature of the male needleless connector.

In one or more embodiments, as shown in FIGS. 15-18, the split-thread protrusion 130 can include one or more cantilevered prongs separated by one or more respective gaps 135, in which at least one of the prongs configure to bend to facilitate interference fit between the protrusion 130 and the mating feature of the male needleless connector or female needleless connector. In one or more embodiments, the cap 110 further includes one or more bridge sections 143 arranged to span between the one or more gaps 135 of the one or more cantilevered prongs of the split-thread protrusion 130.

The sidewall of the removable insert 130 comprises an upper portion and an lower portion. In one or more embodiments, as shown in FIGS. 15-19, the upper portion of the sidewall can tapered outward toward the distal wall and the lower portion of the sidewall can be cylindrical.

As shown in FIG. 15-18, to provide a better rigidity, in an embodiment according to the present disclosure, bridge sections 143 can be arranged between at least parts of the prongs 144 or optionally between all of the prongs 144. A bridge section 143 is generally formed from the same material as the prongs 144 and housing 120. In one or more embodiments, prongs 44 and bridge sections 143 are molded as a whole piece. The bridge sections 143 provide for improved rigidity, giving structural integrity to prongs 144 and permit less material to be used during the manufacturing step of the cap. A good rigidity is achieved when the bridge sections are arranged substantially between the distal ends of the prongs 144.

Figure 19:
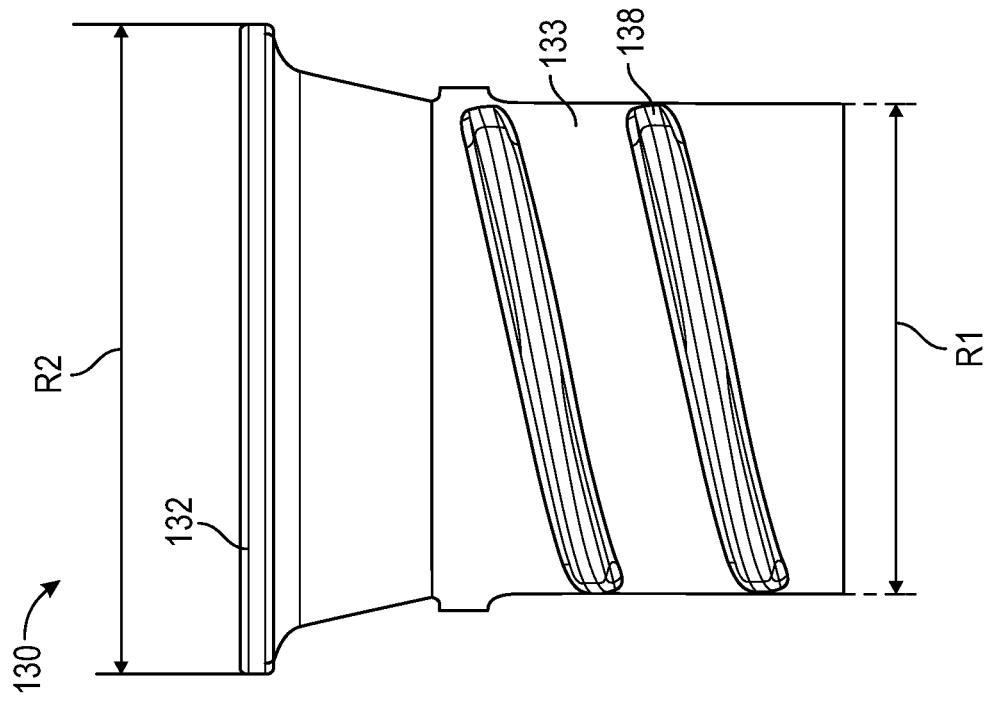
FIG. 19 illustrates a side view of an exemplary removable insert according to one or more embodiments of a second aspect of the disclosure.
Figure 18:
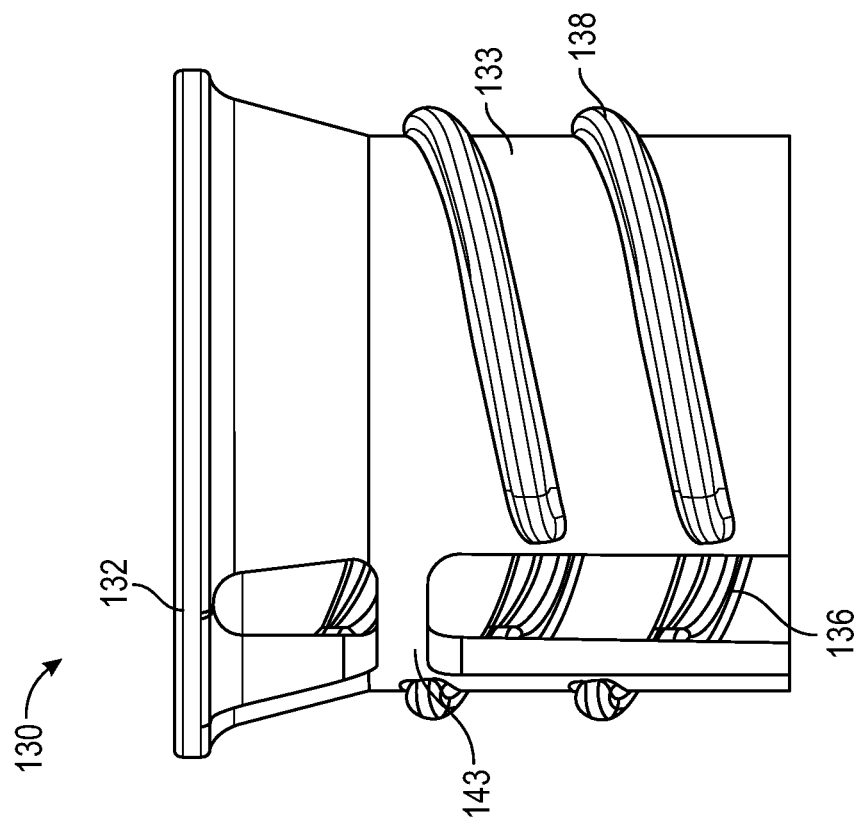
FIG. 18 illustrates a side view of an exemplary removable insert according to one or more embodiments of a second aspect of the disclosure.
Figure 22:
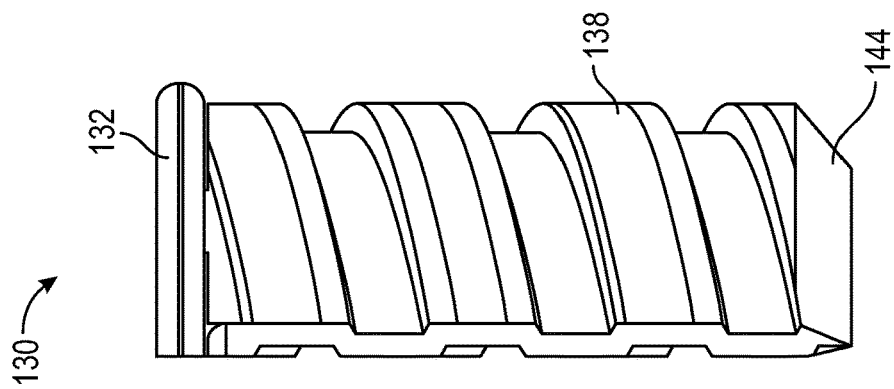
FIG. 22 illustrates a side view of the outer thread pattern of an exemplary removable insert according to one or more embodiments of a second aspect of the disclosure.
Figure 21:
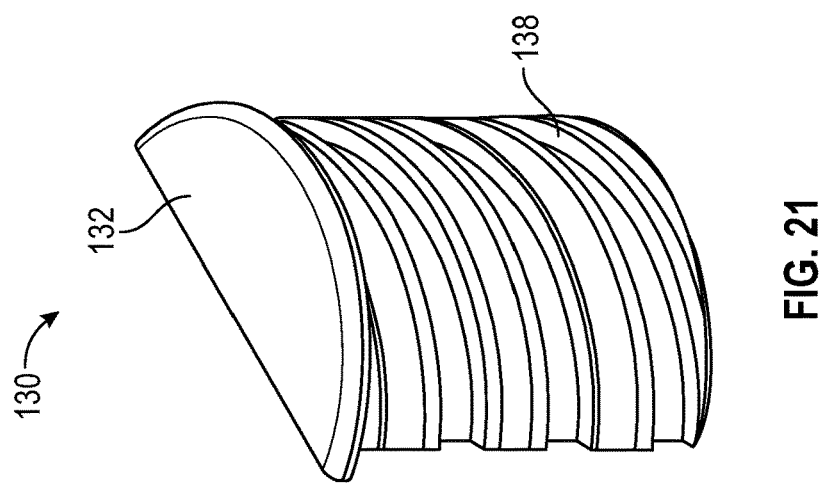
FIG. 21 illustrates a cross sectional view of the outer thread pattern of an exemplary removable insert according to one or more embodiments of a second aspect of the disclosure.
Figure 20:
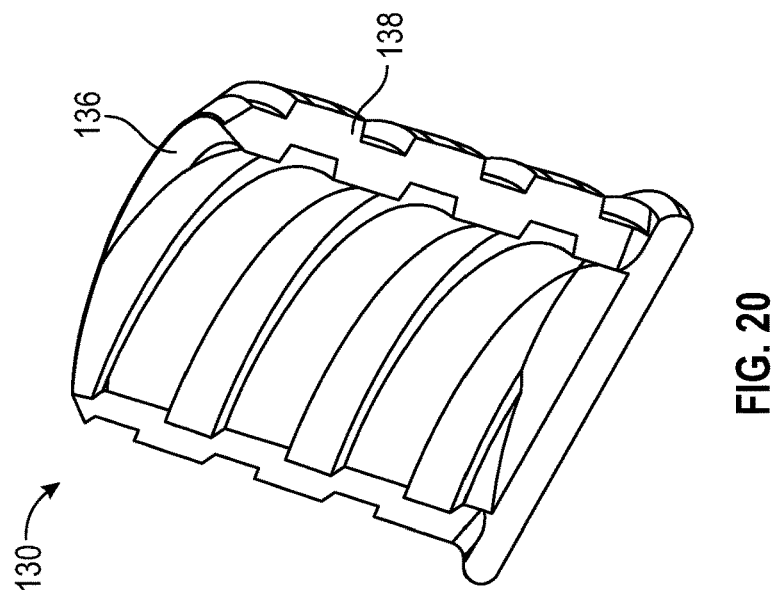
FIG. 20 illustrates a cross sectional view of the inner thread pattern of an exemplary removable insert according to one or more embodiments of a second aspect of the disclosure.

FIG. 19 shows the cap with a view along the centre axis A and from above. As is noted, the sidewall of split-thread insert 130 has a radius $R_1$, which substantially corresponds to a radius of the neck element of a male or female connector. The sidewall of the split-thread insert 130 tapers outwardly and extends to a radius $R_2$ which is larger than the radius $R_1$ of the split-thread insert 130. The radius $R_2$ corresponds substantially to the largest radius of the split-thread insert 130 where a lip is formed to attach the split-thread insert 130 to a recess formed in the inner surface of the housing 120.

In an exemplary implementation of embodiments of the present disclosure, protrusion 130 can be cantilevered, for example by having one or more gaps or cutouts 135. In an exemplary implementation, at least a portion of the a cantilevered protrusion 130 may bend in order to allow better interference fit compliance with the fitting such as at least one of male connector or female connector.

In yet another exemplary implementation, protrusion 130 can extend essentially from inner surface 125 of top wall 122 toward bottom of housing 120.

In still further exemplary implementation, protrusion 130 can extend essentially parallel to sidewall 126.

Figure 33:
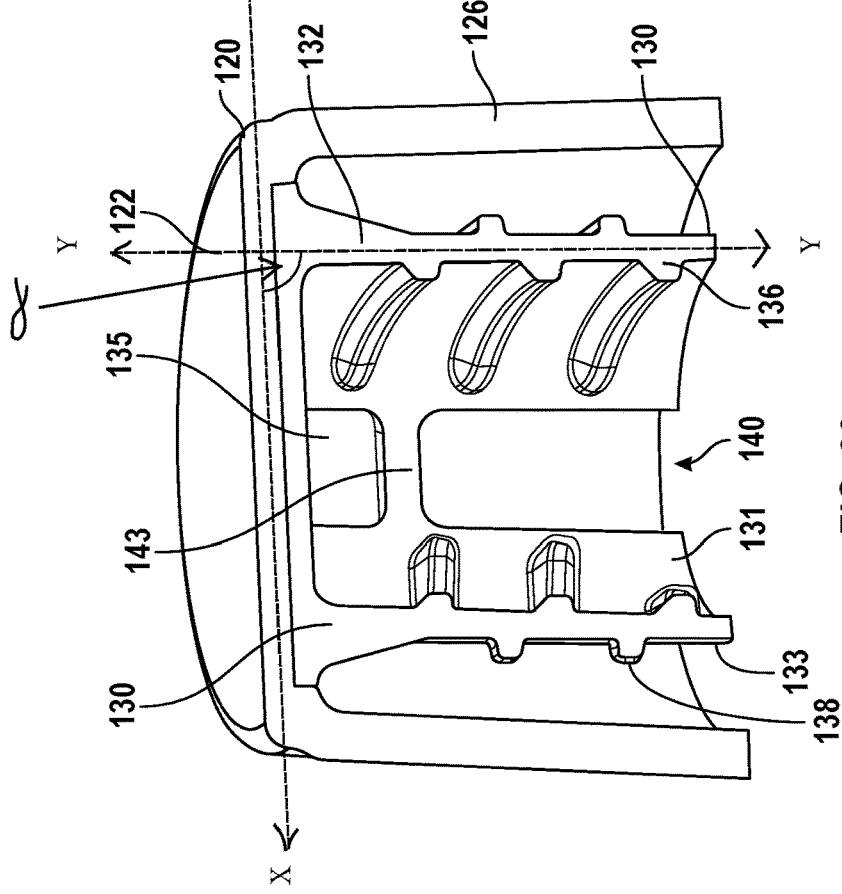
FIG. 33 illustrates a cross-sectional view of a removable insert having an exemplary bridge according to one or more embodiments of a second aspect of the disclosure.

In yet further exemplary implementation, inner portion 132 of cavity 128 can extend further into the cap toward inner surface 125 of top wall 122 than the outer portion 134 which terminates at top, for example as illustrated in the cross section views of FIG. 33.

In still yet further exemplary implementation, a profile of the inner thread 136 and/or the inner surface 131 can essentially parallel, or coincide with, a profile of the outer thread 138 and/or the outer surface 133, respectively.

In an exemplary implementation of FIGS. 15-18, protrusion 130 is illustrated as comprising two prongs spaced by cutouts 135 and extending essentially from surface 125 of top wall 122. However, also within the scope of the disclosure are caps comprising a unitary protrusion 130 without any cutouts 135, and caps having protrusion 130 comprising any number of identical and/or different (in any dimensional characteristics, such as length width, thickness, or shape) prongs, as long as protrusion 130 is configure to engage a female connector with respect to its inner surface, and engage a male connector with respect to its outer surface.

FIGS. 20-24 show a cross-section view of the split-thread protrusion 130 showing the thread pattern of internal thread 136 and outer thread 138.

As shown in FIGS. 20-28, outer threads 138 on the outer sidewall of the split-thread insert 130 extend in a helical pattern.

Figure 24:
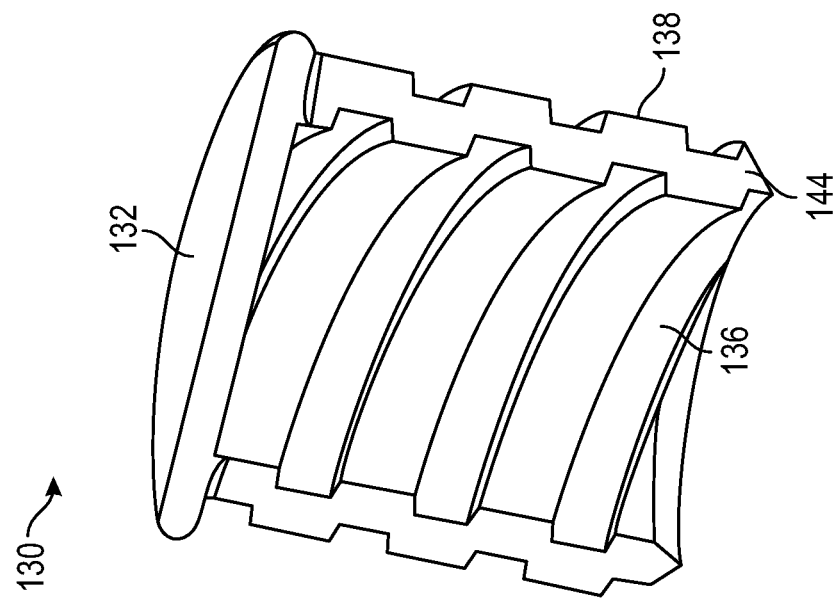
FIG. 24 illustrates a cross sectional view of the thread pattern to illustrate the profile of the thread pattern of an exemplary removable insert according to one or more embodiments of a second aspect of the disclosure.
Figure 23:
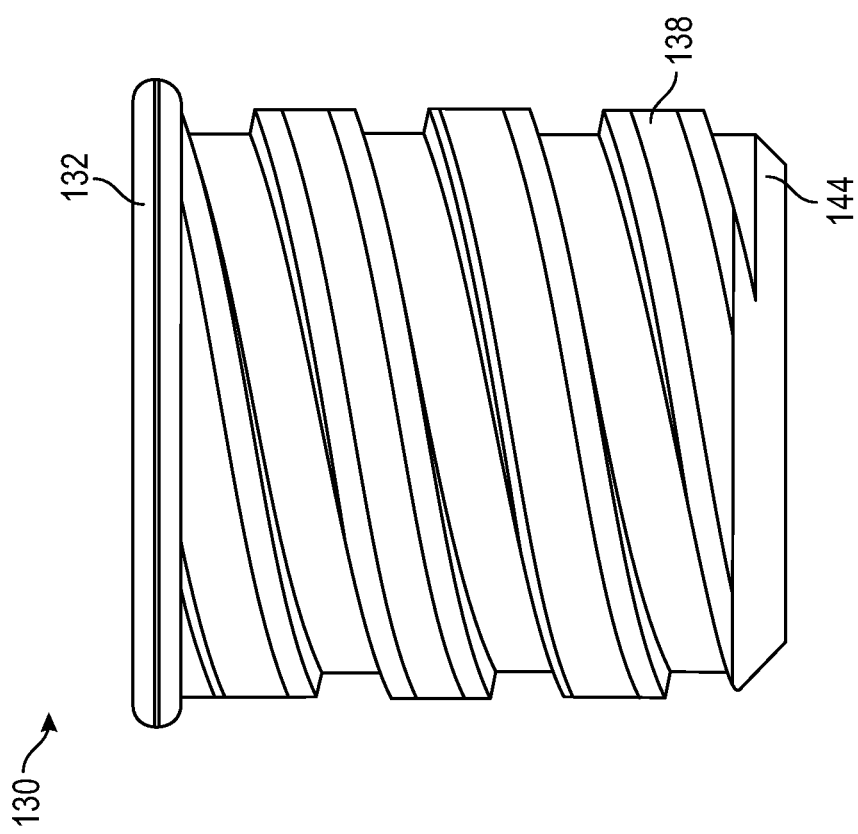
FIG. 23 illustrates a side view of the outer thread pattern of an exemplary removable insert according to one or more embodiments of a second aspect of the disclosure.
Figure 26:
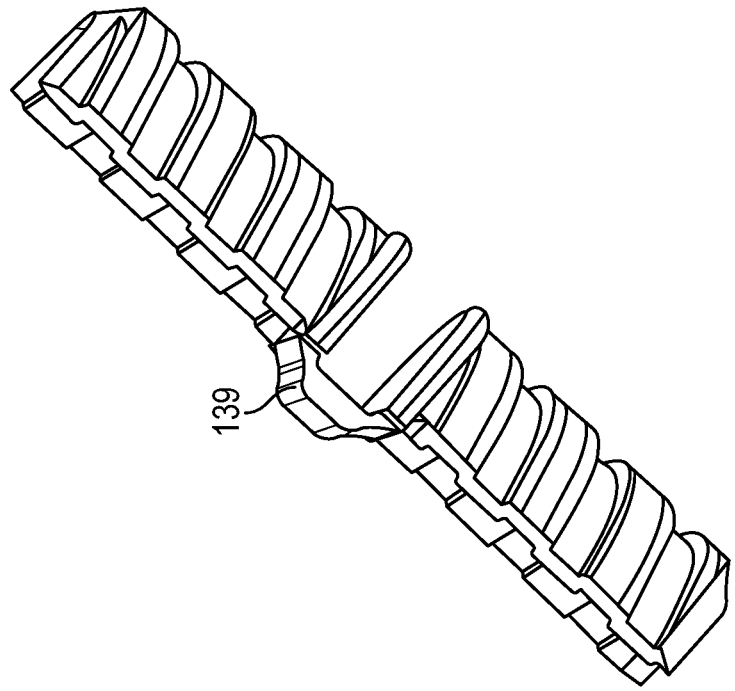
FIG. 26 illustrates a cross sectional view of two inserts being joined by a connecting according to one or more embodiments of a second aspect of the disclosure.
Figure 25:
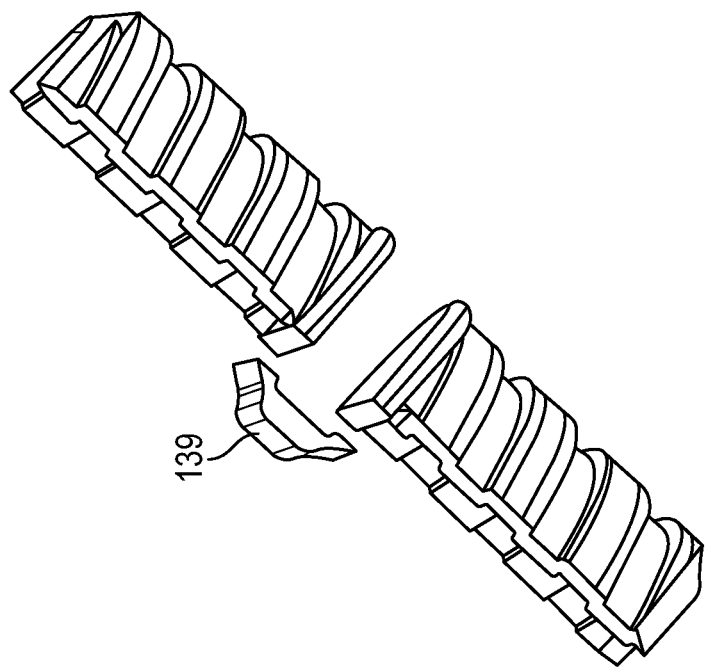
FIG. 25 illustrates a cross sectional view of two inserts and a connecting member according to one or more embodiments of a second aspect of the disclosure.
Figure 28:
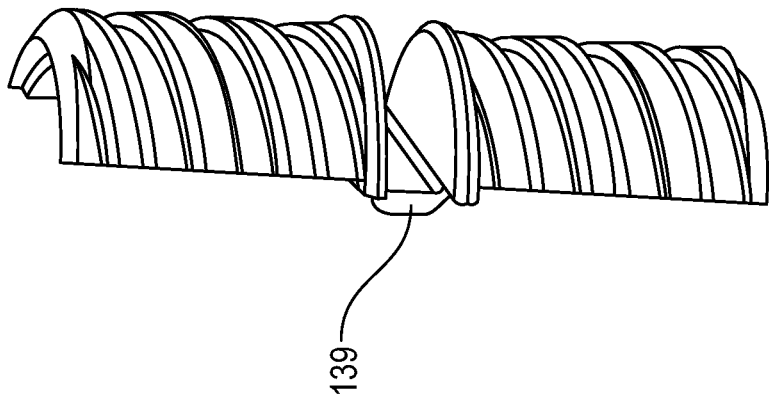
FIG. 28 illustrates a cross sectional side view of two inserts being joined by a connecting according to one or more embodiments of a second aspect of the disclosure.
Figure 27:
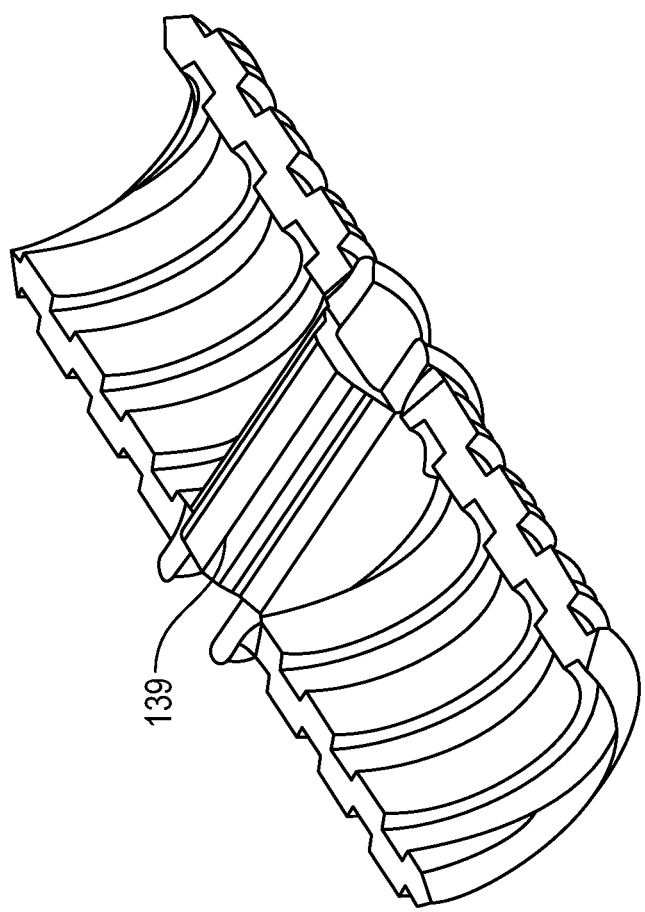
FIG. 27 illustrates a cross sectional view of two inserts being joined by a connecting according to one or more embodiments of a second aspect of the disclosure.

As shown in FIGS. 24 and 27, inner threads 136 on the inner sidewall of the split-thread insert 130 extend in a helical pattern.

As shown in FIGS. 25-28, two or more removable insert 130 may be joined together by a connecting member 139.

Figure 30:
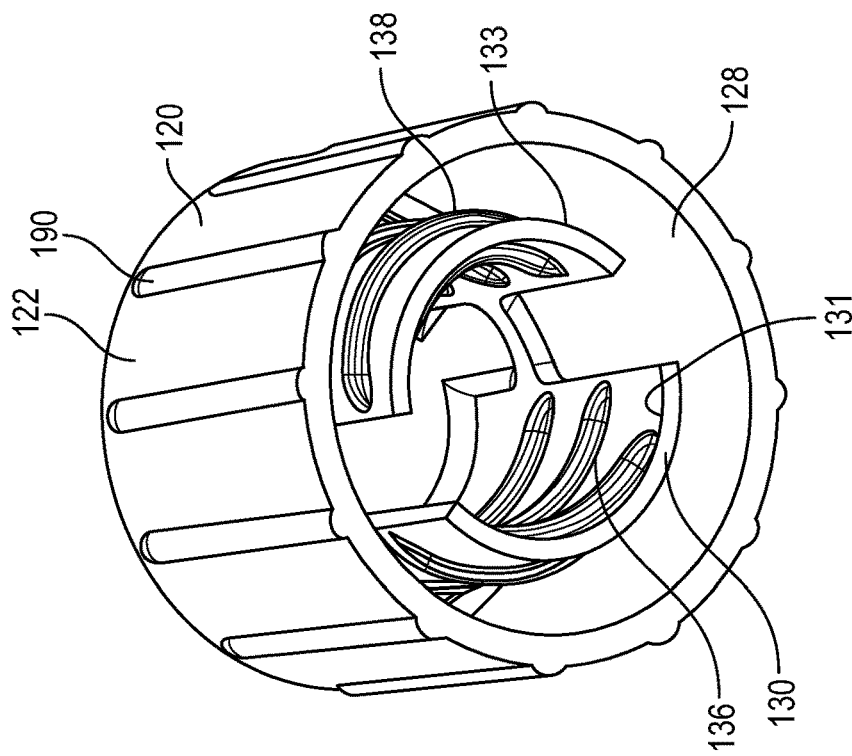
FIG. 30 illustrates a perspective bottom view of a removable insert and positioned within the first cavity according to one or more embodiments of a second aspect of the disclosure.
Figure 29:
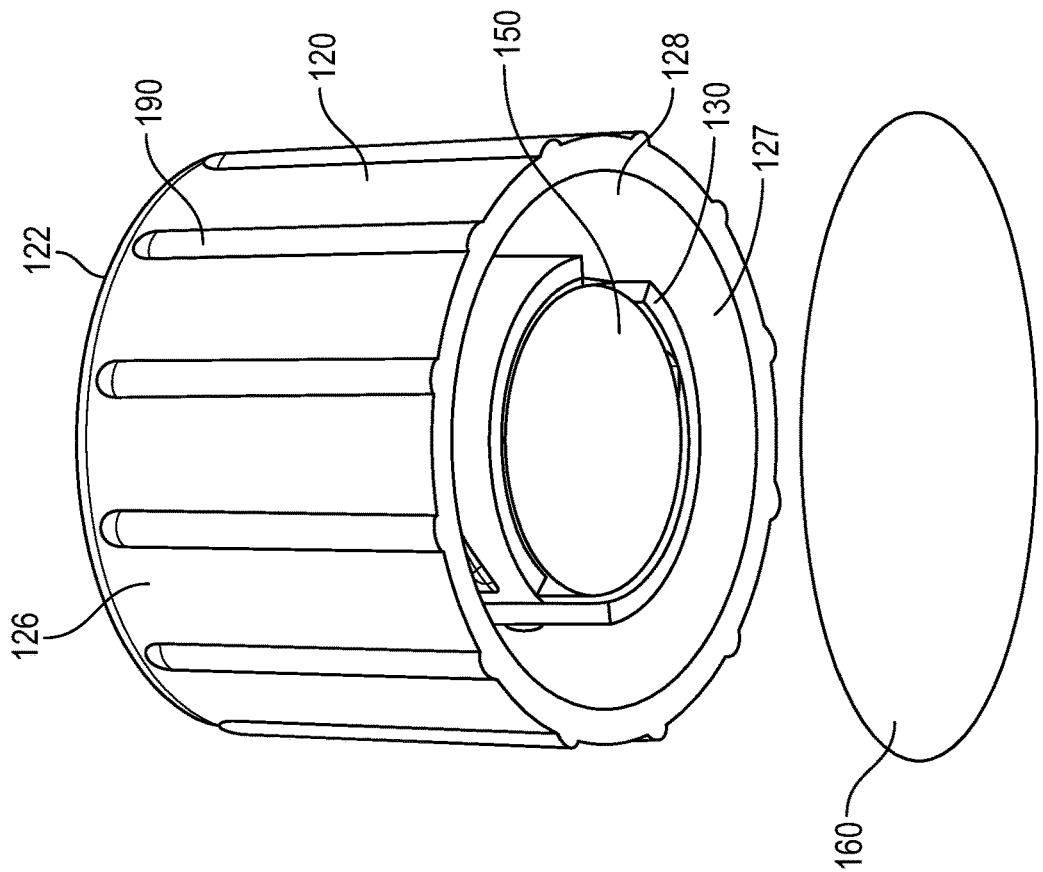
FIG. 29 illustrates a perspective view of a removable insert and absorbent material positioned within the first cavity according to one or more embodiments of a second aspect of the disclosure.

As shown in FIGS. 29-30, the removable insert 130 can be positioned within the first cavity 128. As shown in FIGS. 29-30, disposed within cavity 128 is a split-thread insert in the form of a protrusion 130 (which can be essentially cylindrical and coaxial with sidewall 126) having an inner surface 131 defining an inner portion 132 of cavity 128, and an outer surface 133 defining and outer portion 134 of cavity 128. Split-thread insert 130 is in the form of a protrusion 130 and comprises an inner thread 136 on its inner surface 131 for engaging a female connector and an outer thread 138 on its outer surface 133 for engaging a male connector.

Figure 31:
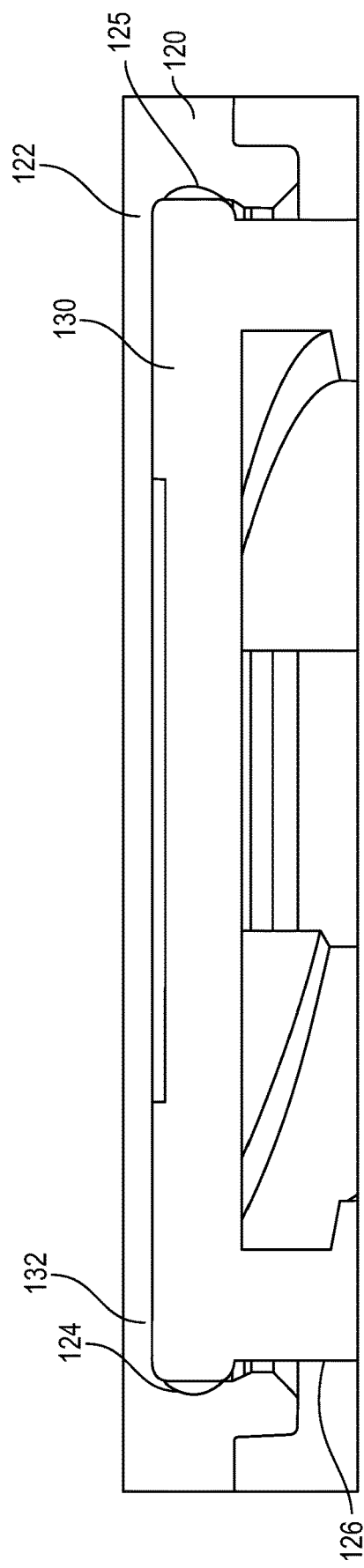
FIG. 31 illustrates a partial cross-sectional view of a removable insert and positioned within the housing of a cap according to one or more embodiments of a second aspect of the disclosure.
Figure 32A:
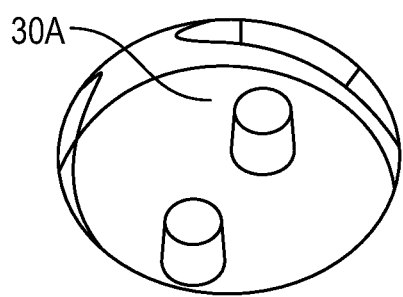
FIGS. 32A-D illustrate geometries that may be present on the top wall or sidewall of the housing or removable insert according to one or more embodiments of a second aspect of the disclosure.
Figure 32B:
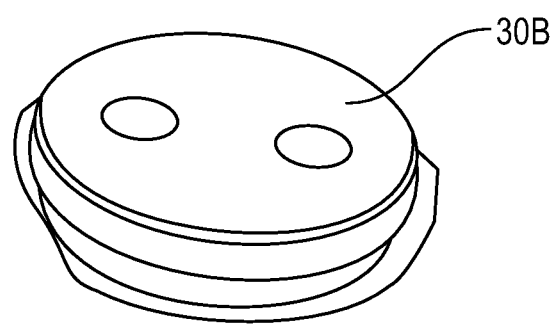
Figure 32C:
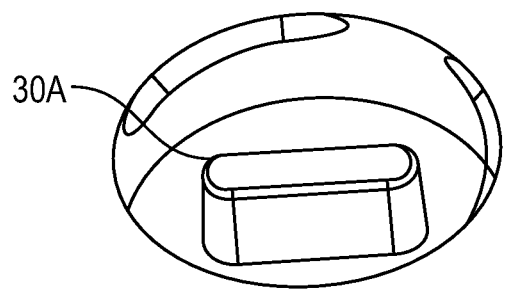
Figure 32D:
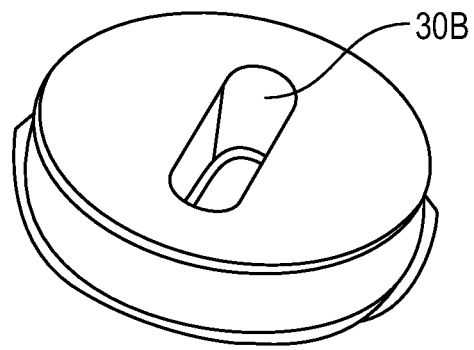

In one or more embodiments, as shown in FIG. 31, split-thread insert 130 and the housing 120 can be bonded together through ultrasonic welding or solvent resistant biocompatible adhesive. As shown in FIGS. 31-38, split-thread insert 130 and the housing 120 can also be interlocked through interference fit or snap fit. A ledge/wedge portions can be arranged at the distal ends of the split-thread insert 130 to provide for a snap on connection to the cap housing. The inner surface 125 of the top wall 122 of housing 120 may have a recess into which the ledge/wedge of the insert may be inserted.

The ledge/wedge portion of the split-thread insert 130 is adapted to lock, temporarily or permanently, into the recess 124 in the inner surface 125 of the top wall 122 of housing 120. As the wedge portion of the split-thread insert 130 is mounted onto the recess 124 in the inner surface 125 of the top wall 122 of housing 120, the recess is deformed and pressed aside. When the wedge portion of the split-thread insert 130 has passed the lip of the recess, the lip of the recess tends to return to its original position, hooking the ledge/wedge portion of the split-thread insert 130 thereby holding the split-thread insert 130 in position on the housing 120.

As shown in FIGS. 32A-D, to prevent insert from rotating relative to the cap body, protrusions such as pins 30A, slots 30B, or other geometries such as tetrahedrons are present on the top wall 122 or sidewall 126 of the housing or the removable insert 130, while corresponding geometries are present on the other to receive the protrusions.

Figure 35:
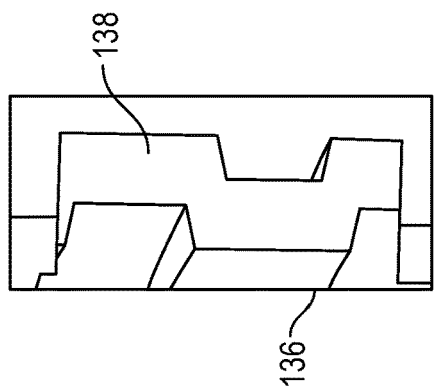
FIG. 35 illustrates a partial view of another exemplary bridge according to one or more embodiments of a second aspect of the disclosure.
Figure 34:
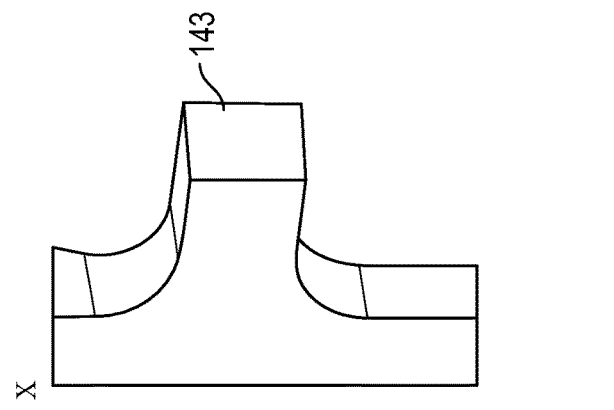
FIG. 34 illustrates a partial view of an exemplary bridge according to one or more embodiments of a second aspect of the disclosure.

As shown in FIGS. 33-35, bridges 143 connecting the gaps 142 between the prongs 144 restrict the angle of the deflection of said prongs 144, increasing the security of engagement when the disinfecting cap is connected to male or female connectors. As shown in FIGS. 33-35, the thickness and width of the bridges 143 can be adjusted to adjust/control the apparent rigidity given a certain material property of the prongs, modifying the desired deflection angle. The thickness of the bridge 143 can be the full or partial sectional thickness of the prongs 144, including or excluding the profile of the threading. With respect to FIG. 33, the shape of the split-thread insert 130 can vary. Split-thread insert 130 may have varying shapes including, but not limited to, the shape of a trapezoid, an inverted trapezoid, a convex inner surface (for example a paraboloid), concave inner surface, or a straight profile (i.e., cylindrical or semi-conical shape). In one or more embodiment, the profile of the split-thread insert 130 and/or the opening of the split-thread insert 130 can vary. In one or more embodiments, the angle α between the distal wall of the split-thread insert 130 and the prongs of the split-thread insert 130, as shown in FIG. 33, can range from 80-100° or 85-95° such that the split-thread insert 130 may have shapes including, but not limited to, have the shape of a trapezoid, an inverted trapezoid. In one or more embodiments, the angle α between the distal wall and prongs of the split-thread insert 130, as shown in FIG. 33, is 90°. In one or more embodiment, the inner diameter of the split-thread insert 130 is cylindrical. In one or more embodiments, the diameter the cavity between the prongs of the split-thread insert 130 increases in a direction from the distal wall of the split-thread insert 130 to the open proximal end of the split-thread insert. In one or more embodiments, the diameter the cavity between the prongs of the split-thread insert 130 decreases in a direction from the distal wall of the split-thread insert 130 to the open proximal end of the split-thread insert. In one or more embodiments, the sidewall of the split-thread insert 130 tapers outward from the distal wall toward the open proximal end. In one or more embodiments, the sidewall of the split-thread insert 130 tapers inward from the distal wall toward the open proximal end.

Figure 38:
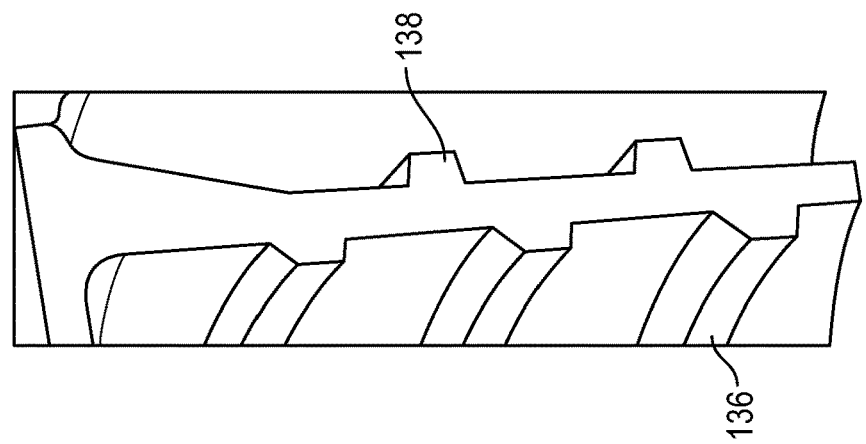
FIG. 38 illustrates a partial view of another exemplary thread pattern according to one or more embodiments of a second aspect of the disclosure.
Figure 37:
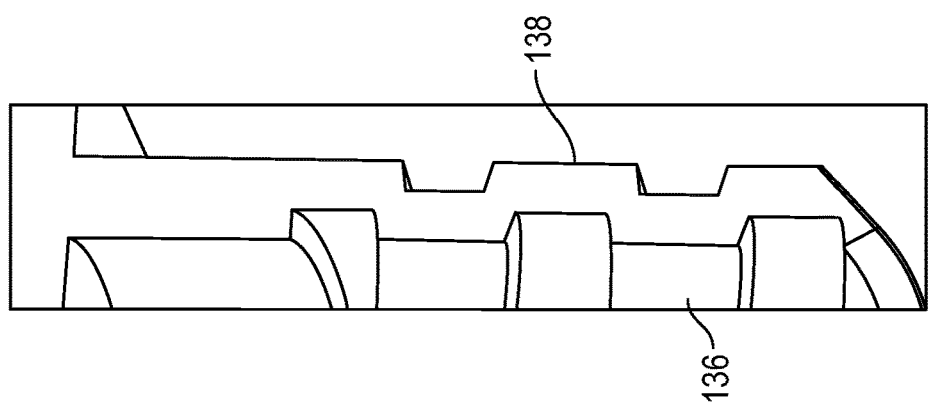
FIG. 37 illustrates a partial view of exemplary thread pattern according to one or more embodiments of a second aspect of the disclosure.
Figure 36:
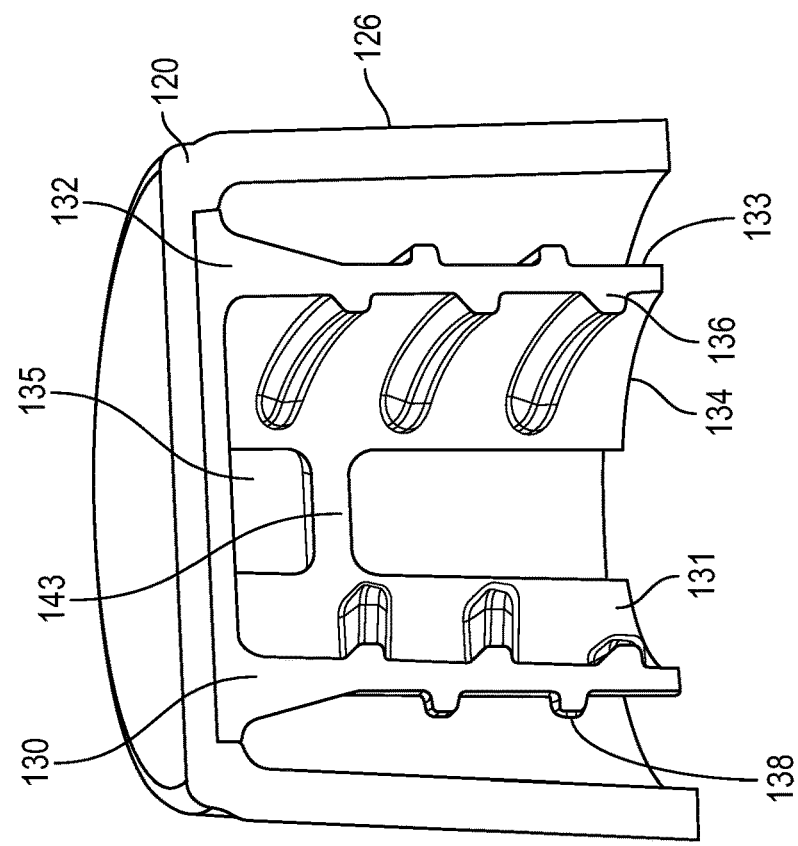
FIG. 36 illustrates a cross-sectional view of a removable insert having an exemplary bridge according to one or more embodiments of a second aspect of the disclosure.
Figure 40:
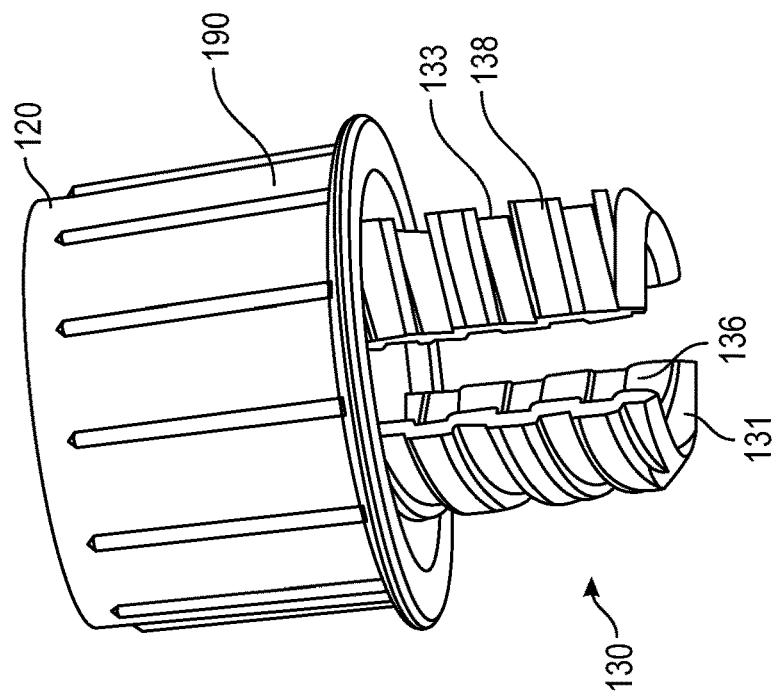
FIG. 40 illustrates an exploded view of a removable insert and positioned within the housing of a cap according to one or more embodiments of a second aspect of the disclosure.
Figure 39:
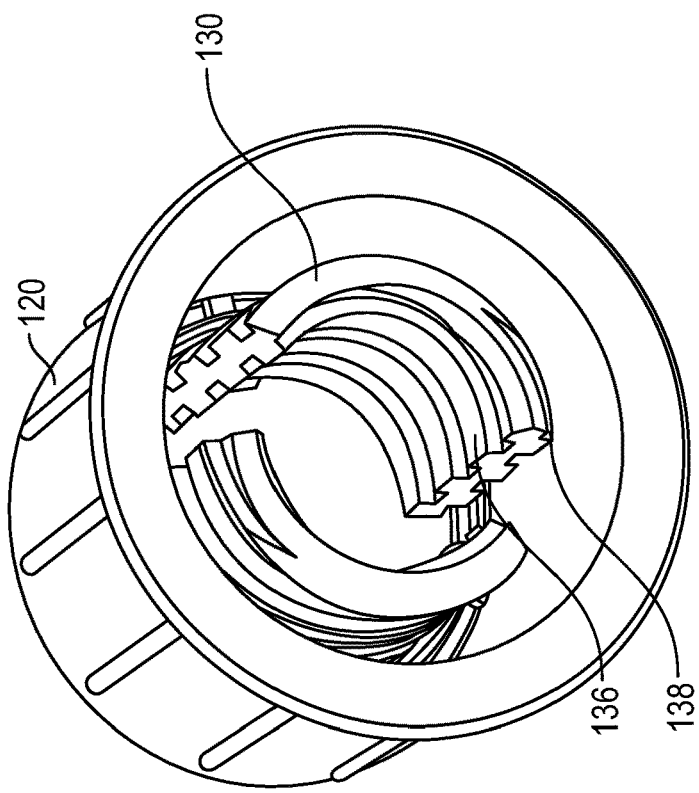
FIG. 39 illustrates a perspective bottom view of a removable insert and positioned within the housing of a cap according to one or more embodiments of a second aspect of the disclosure.
Figure 42:
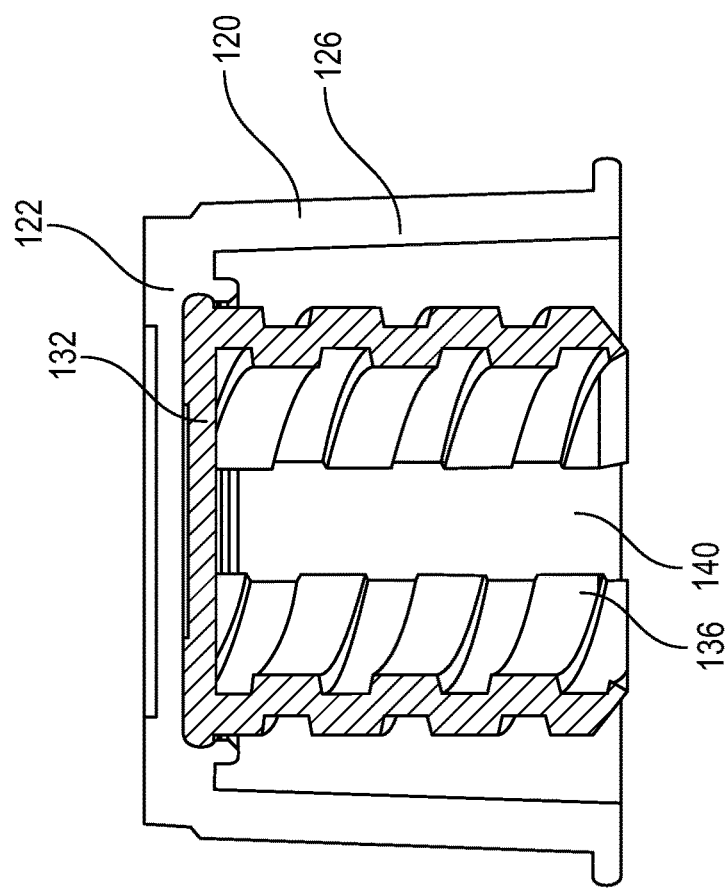
FIG. 42 illustrates a cross-sectional side view of a removable insert and positioned within the housing of a cap according to one or more embodiments of a second aspect of the disclosure.
Figure 41:
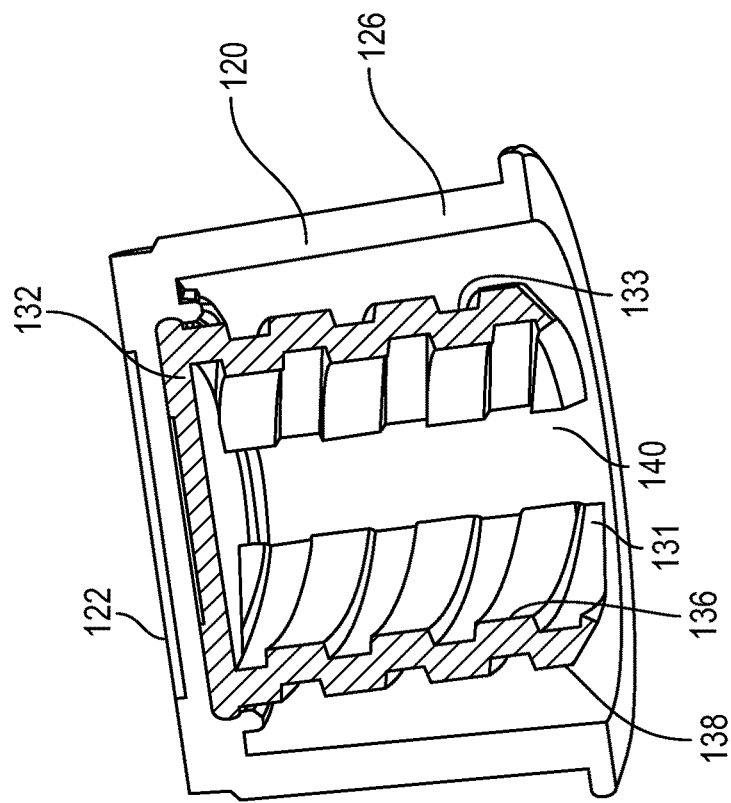
FIG. 41 illustrates a cross-sectional view of a removable insert and positioned within the housing of a cap according to one or more embodiments of a second aspect of the disclosure.

As shown in FIGS. 36-38, full length or partial length of the prongs 144 may be threaded to control how deep the connectors can be threaded into the cavity. This may also facilitate the volume of compression on IPA impregnated sponges to control the IPA volume that's dispensed upon engagement to connectors.

In yet another exemplary implementation, as shown in FIG. 29, an absorbent material 150 serves as a disinfecting member, such as an IPA soaked sponge and/or sponge. In one or more embodiments, absorbent material 150 may be in the form of one or more sponge(s) formed together as a single cleaning member or formed separate as multiple cleaning members, can be provided within cavity 128, for example in the proximity of inner surface 125 of top wall 122 of inner portion 132 and/or towards top of outer portion 134 of cavity 128.

The cap 110 can achieve disinfection when used on luer connectors by integrating disinfectant or antimicrobial agent in the cavity 128 of the cap 110. The disinfectant or antimicrobial agent can be directly included in the chamber 112 or disinfectant or antimicrobial agent can be absorbed into sponges or foam material that fills the chamber of cap 110. Cap 110 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 150 toward the top wall 122 of housing 120 upon connection to the female luer connector or the male luer connector allows the connector to contact the disinfectant or antimicrobial agent to disinfect the female luer connector or the male luer connector.

In an exemplary implementation, a peel sealing film 160 can be provided to seal the opening 127 prior to use of cap 110, for example, by attachment to a surface of a rim 129 of an open bottom 123 of housing 120, as described for example in the above-referenced prior applications.

Referring to FIGS. 29-30, according to exemplary embodiments of the disclosure, cap 110 can receive a tip or hub of a female needleless connector, for example after a peel seal 160 is removed or when the peal seal is pierced, within inner portion 132 of cavity 128 and secure (for example, threadedly) the tip of needleless connector within inner portion 132 of cavity 128. One or more threads 136 can be sufficient to interlock with a mating feature (such as one or more protrusions, lugs and/or thread) of a hub or tip of needleless connector.

According to exemplary embodiments of the disclosure, cap 110 can receive a tip or hub of a male needleless connector, for example after a peel seal 150 is removed or when the peal sealing film is pierced, within inner portion 132 of cavity 128 and secure the tip or hub of needleless connector within the inner portion of cavity 128, by securing (for example, threadedly) collar of connector within outer portion of cavity 128. One or more threads 138 can be sufficient to interlock with a mating feature 186 (such as one or more protrusions, lugs and/or thread) of collar 184 of needleless connector 180.

The cap 110 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 110 comprises a polypropylene or polyethylene material.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

A third aspect of the present disclosure relates to a cap 210 including a housing 220, a removable insert 230, an absorbent material 250, a disinfectant or an antimicrobial agent and a septum 262, as shown in FIGS. 43-50.

In one or more embodiments, embodiments of the housing, removable insert, absorbent material, disinfectant or antimicrobial agent may be the same as described above for the second aspect of the present disclosure.

Figure 44:
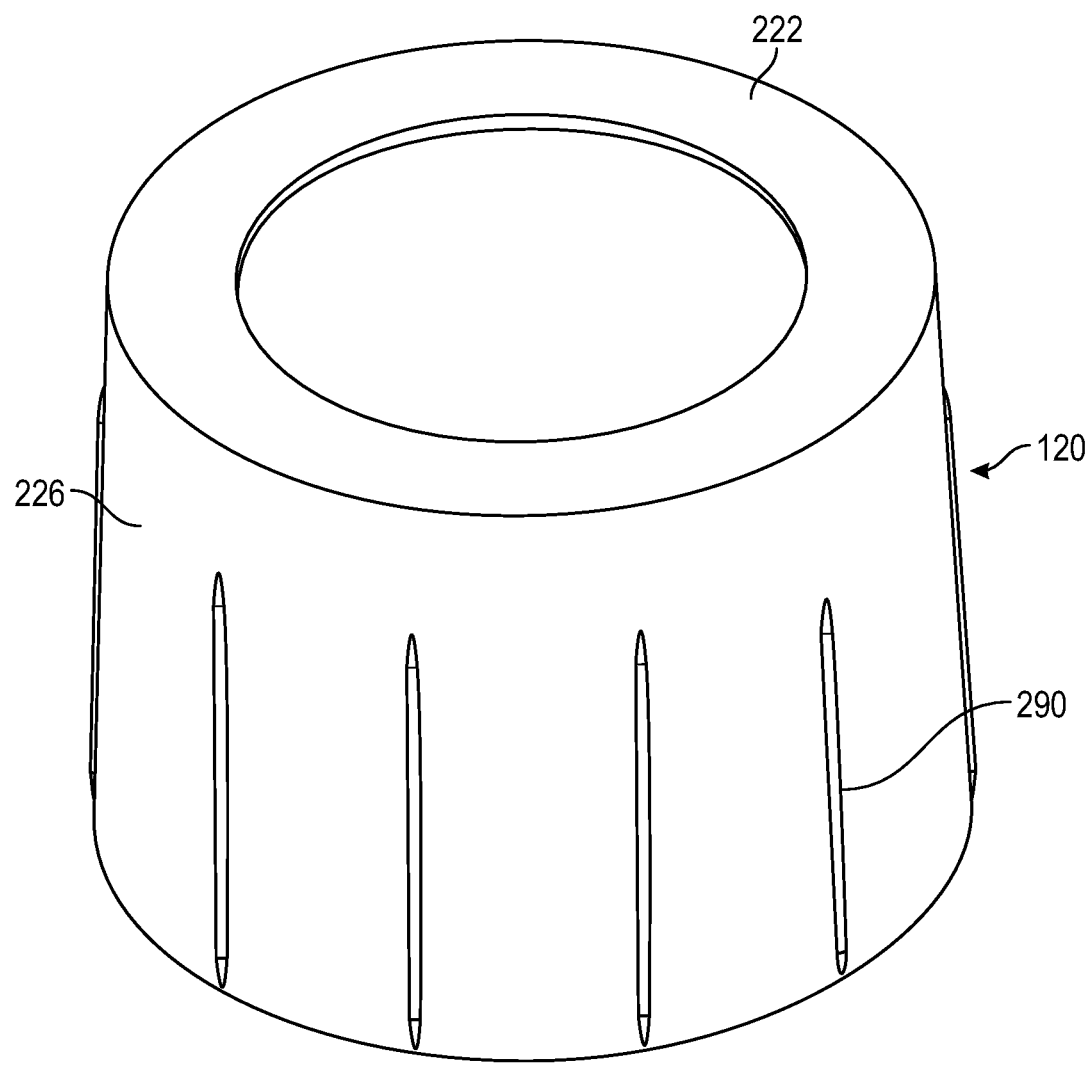
FIG. 44 illustrates a perspective view of an exemplary cap according to one or more embodiments of a third aspect of the disclosure.
Figure 46:
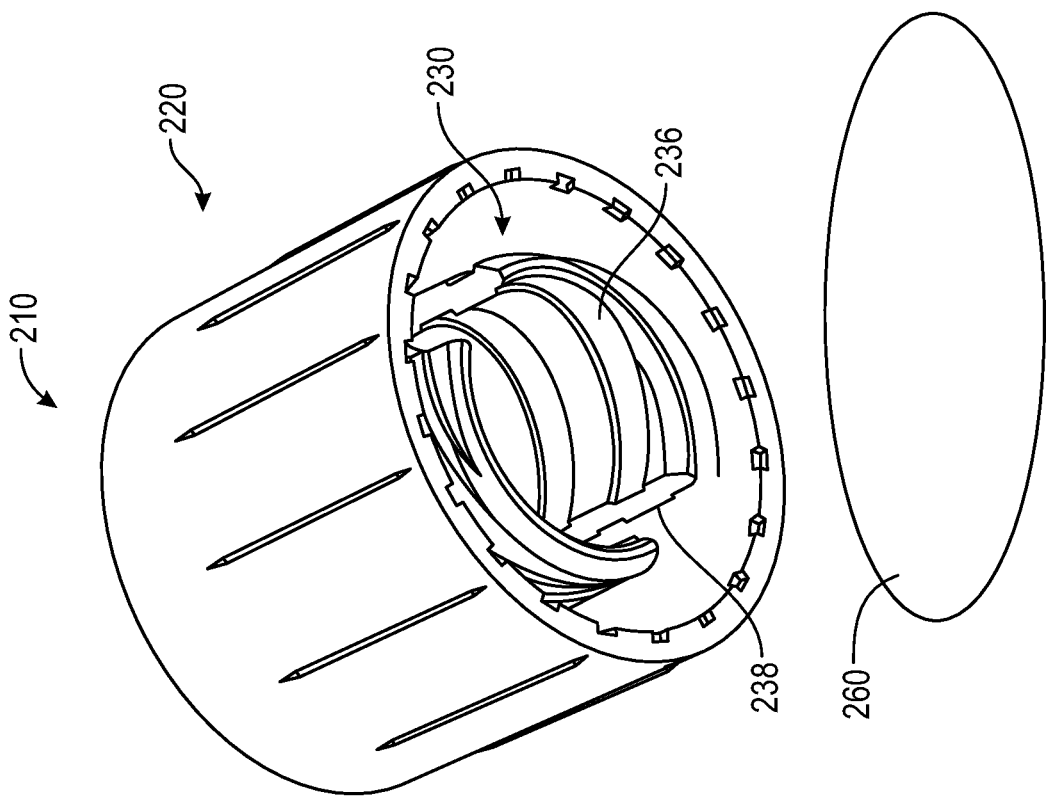
FIG. 46 illustrates a perspective bottom view of an exemplary cap according to one or more embodiments of a third aspect of the disclosure.
Figure 45:
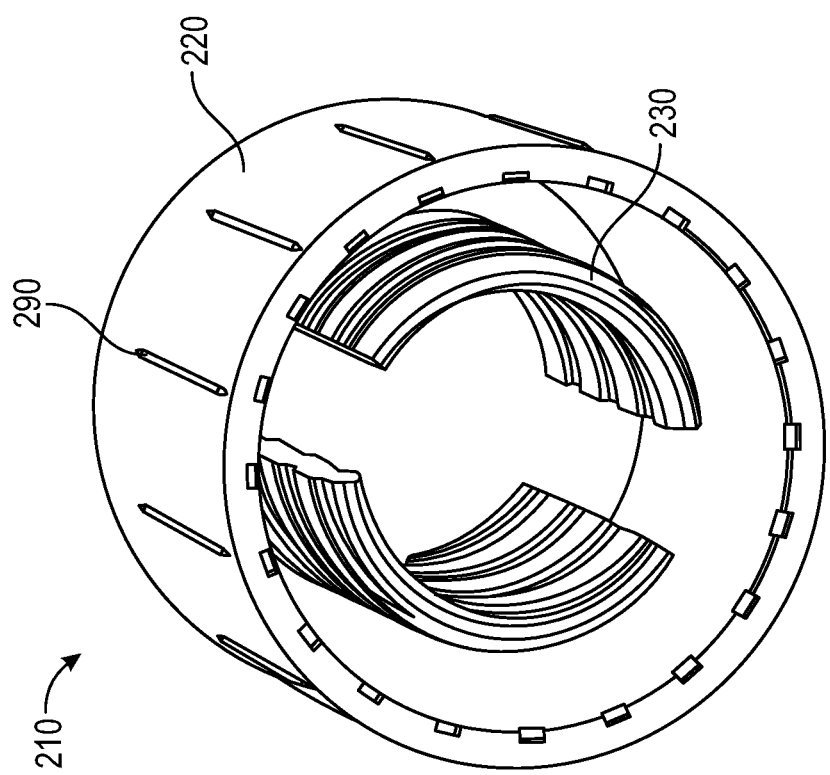
FIG. 45 illustrates a perspective bottom view of an exemplary cap according to one or more embodiments of a third aspect of the disclosure.

In one or more embodiments, as shown in FIGS. 44-46, the housing 220 comprises a top wall 222, an essentially cylindrical sidewall 226 forming a first cavity 228, and an open bottom 223 formed by the cylindrical sidewall 226 with an opening to the first cavity 228 within the housing 220 for receiving a hub of a female needleless connector or a male needleless connector. In one or more embodiments, the removable insert 230 can be positioned within the first cavity 228. In one or more embodiments, the removable insert 230 comprises a closed distal end comprising a distal wall, an open proximal end, a sidewall extending proximally from the distal wall toward the open proximal end. In one or more embodiments, the sidewall comprises a split-thread protrusion integrally formed with the distal wall, the split-thread protrusion having an inner surface 231 and an outer surface 233. In one or more embodiments, the inner surface 231 of the split-thread protrusion defines a second cavity 240. In one or more embodiments, an inner thread 236 can be disposed on the inner surface 231 of the split-thread protrusion, the inner thread 236 being sufficient to interlock with a mating feature of the female needleless connector. In one or more embodiments, an outer thread 238 is disposed on the outer surface 233 of the split-thread protrusion 230, the outer thread 238 being sufficient to interlock with a mating feature of the male needleless connector.

In one or more embodiments, as shown in FIG. 43A and FIG. 43B, the split-thread protrusion 230 comprises one or more cantilevered prongs separated by one or more respective gaps 235. In one or more embodiments, at least one of the prongs configure to bend to facilitate interference fit between the protrusion and the mating feature of the male needleless connector or female needleless connector.

In one or more embodiments, the cap 210 further includes one or more bridge sections 243 arranged to span between the gaps 235 of the one or more cantilevered prongs of the split-thread protrusion.

In one or more embodiments, the sidewall of the insert 230 comprises an upper portion and a lower portion. In one or more embodiments, the upper portion of the sidewall can be tapered outward toward the distal wall and the lower portion of the sidewall can be cylindrical.

Referring to FIGS. 43-50, according to exemplary embodiments of the present disclosure a cap 210 comprises a housing 220 which includes a top wall 222 with an inner surface 225, a sidewall 226 (which can be essentially cylindrical) with an inner surface 221, and an opening 227 into a cavity 228. Opening 227 is disposed at bottom 223 of housing 220. Inner surface 225 of top wall 222 can form a top of cavity 228. Disposed within cavity 228 is a protrusion 230 (which can be essentially cylindrical and coaxial with sidewall 226) having an inner surface 231 defining an inner portion 232 of cavity 228, and an outer surface 233 defining and outer portion 234 of cavity 228. Protrusion 230 comprises an inner thread 236 on its inner surface 231 for engaging a female connector and an outer thread 238 on its outer surface 233 for engaging a male connector.

In an exemplary implementation, as shown in FIG. 46, a peel seal 260 can be in the form of a film and be provided to seal the opening 227 prior to use of cap 210, for example, by attachment to a surface of a rim 229 of an open bottom 223 of housing 220, as described for example in the above-referenced prior applications.

The rim 229 of an open bottom 223 of housing 220 may comprise a peripheral ledge extending radially outward from the annular sidewall 226 at the open bottom 223 defining an end face. The surface of rim 229 of an open bottom 223 of housing 220 also defines an engagement surface where a peelable seal 260 may be secured.

Referring to FIG. 46, in one or more embodiments, the peelable seal 260 is disposed on the engagement surface of open bottom 223 of housing 220 to prevent the disinfectant or the antimicrobial agent from exiting the cavity 228. With the absorbent material 250 properly inserted into the cavity 228 of the cap 210, the peelable seal 260 may be secured to the engagement surface of open bottom 223 of housing 220. The peelable seal 260 minimizes entry of potential particulate hazard and also provides a substantially impermeable enclosure for the cap 210, provides a leak prevention and protection enclosure, protects the contents of absorbent material 250 contained within the cavity 228, and/or maintains a sealed, sterilized environment. The peelable seal 260 provides a sufficient seal at a range of temperatures, pressures, and humidity levels. In one or more embodiments, the peelable seal 260 comprises an aluminum or multi-layer polymer film peel back top. In a specific embodiment, the peelable seal 260 is heat-sealed or induction sealed to the end face of the locking lid or to the cap open end. In one or more embodiments, the peelable seal 260 comprises a moisture barrier.

In yet another exemplary implementation, absorbent material 250 is a disinfecting member or members in the form of a IPA soaked sponge that can be provided within cavity 228, for example in the proximity of inner surface 225 of top wall 222 of inner portion 232 and/or towards top 239 of outer portion 234 of cavity 228, for example as described in the second aspect of the present disclosure.

The cap 210 can achieve disinfection when used on luer connectors by integrating disinfectant or antimicrobial agent in the cavity 228 of the cap 210. The disinfectant or antimicrobial agent can be directly included in the chamber 212 or disinfectant or antimicrobial agent can be absorbed into sponges or foam material that fills the chamber of cap 210. Cap 210 is designed to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

Compression of the absorbent material 250 toward the top wall 222 of housing 220 upon connection to the female luer connector or the male luer connector allows the connector to contact the disinfectant or antimicrobial agent to disinfect the female luer connector or the male luer connector.

In an exemplary implementation of embodiments of the present disclosure, protrusion 230 can be cantilevered, for example by having one or more cutouts or gaps 235. In an exemplary implementation, at least a portion of the a cantilevered protrusion 230 may bend in order to allow better interference fit compliance with the fitting such as at least one of male connector or female connector.

In yet another exemplary implementation, protrusion 230 can extend essentially from inner surface 225 of top wall 222 toward bottom of housing 220.

In still further exemplary implementation, protrusion 230 can extend essentially parallel to sidewall 226. In yet further exemplary implementation, inner portion 232 of cavity 228 can extend further into the cap toward inner surface 225 of top wall 222 than the outer portion 234 which terminates at top 239. In still yet further exemplary implementation, a profile of the inner thread 236 and/or the inner surface 231 can essentially parallel, or coincide with, a profile of the outer thread 238 and/or the outer surface 233, respectively.

Figure 48:
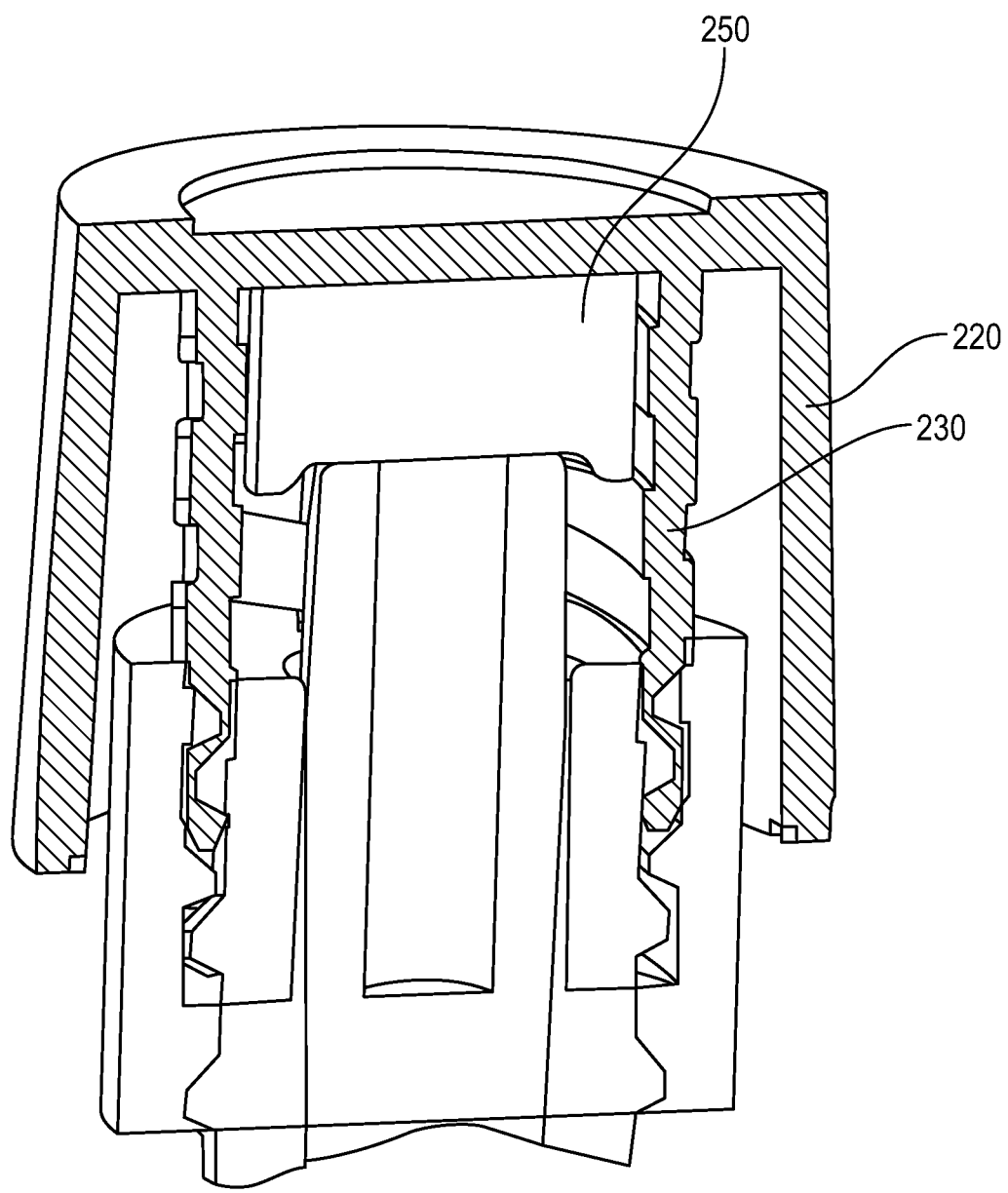
FIG. 48 illustrates a cross-sectional view of an exemplary cap according to one or more embodiments of a third aspect of the disclosure connected to an exemplary medical connector.

Referring to FIG. 48, according to exemplary embodiments of the disclosure, cap 220 can receive a tip or hub 272 of a female needleless connector 270, for example after a peel sealing film sealing cavity 228 is removed or when the peal sealing film is pierced, within inner portion 232 of cavity 228 and secure (for example, threadedly) the tip of needleless connector 270 within inner portion 232 of cavity 228. One or more threads 236 can be sufficient to interlock with a mating feature 274 (such as one or more protrusions, lugs and/or thread) of a tip or hub 272 of needleless connector 270, as described for example in related U.S. patent application Ser. Nos. 15/408,278 and 15/408,187, both filed on Jan. 17, 2017

Figure 47:
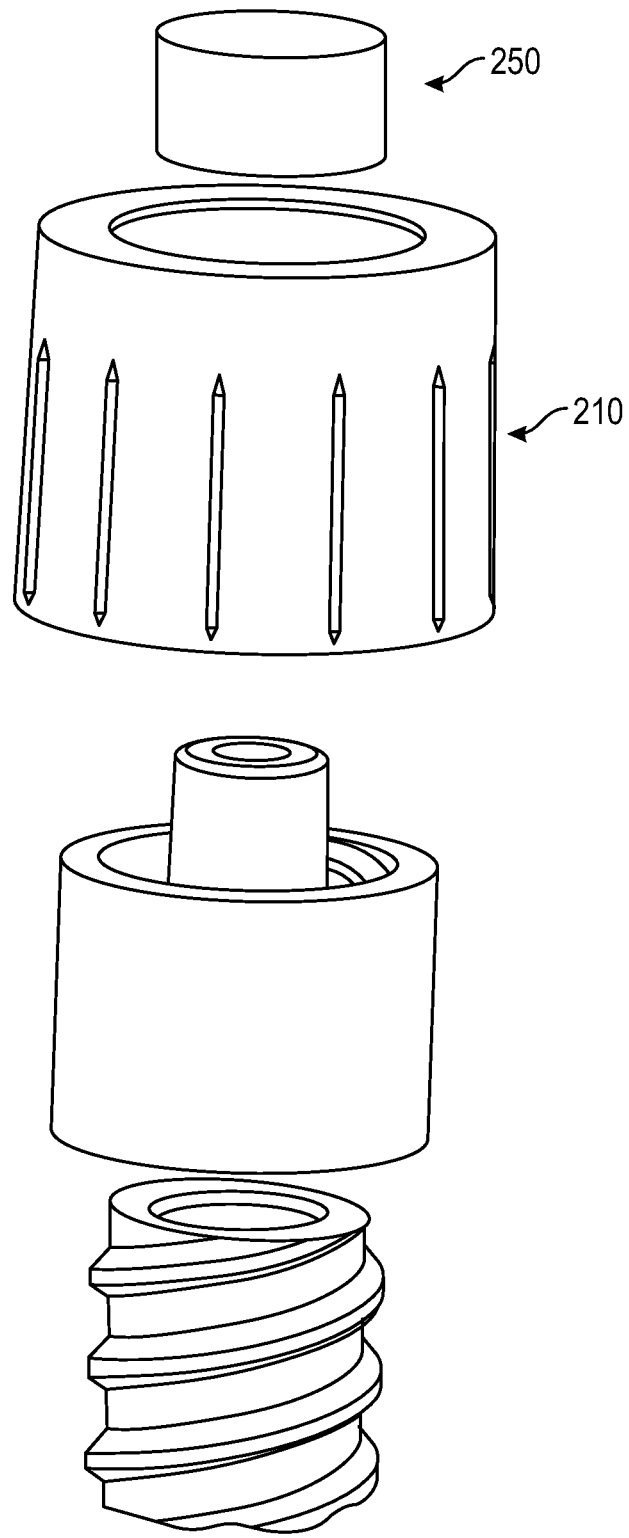
FIG. 47 illustrates a exploded view of an exemplary cap according to one or more embodiments of a third aspect of the disclosure and a medical connector.

Referring further to FIGS. 47-48, according to exemplary embodiments of the disclosure, cap 220 can receive a tip or hub 282 of a male needleless connector 280, for example after a peel sealing film sealing cavity 228 is removed or when the peal sealing film is pierced, within inner portion 232 of cavity 228 and secure the tip or hub 282 of needleless connector 280 within the inner portion 232 of cavity 228, by securing (for example, threadedly) collar 284 of connector 280 within outer portion 234 of cavity 228. One or more threads 238 can be sufficient to interlock with a mating feature 286 (such as one or more protrusions, lugs and/or thread) of collar 284 of needleless connector 280.

In an exemplary implementation of FIG. 43B, protrusion 230 is illustrated as comprising two prongs spaced by cutouts or gaps 235 and extending essentially from surface 225 of top wall 222. However, also within the scope of the disclosure are caps comprising a unitary protrusion 230 without any cutouts or gaps 235, and caps having protrusion 230 comprising any number of identical and/or different (in any dimensional characteristics, such as length width, thickness, or shape) prongs, as long as protrusion 230 is configure to engage a female connector with respect to its inner surface, and engage a male connector with respect to its outer surface.

Referring to FIGS. 44-46, in one or more embodiments, the exterior surface of sidewall 226 comprises a plurality of grip members 290.

The cap 210 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the cap 210 comprises a polypropylene or polyethylene material.

In one or more embodiments, when a hub of the female needleless connector is received within the inner surface of the second cavity (40, 140, 240), the hub is secured within the inner surface of the second cavity (40, 140, 240) by interlocking at least a portion of the inner thread with a mating feature on the hub of the female needleless connector. In one or more embodiments, when a hub of the male needleless connector is received within the inner surface of the second cavity (40, 140, 240), the hub is secured within the first cavity by interlocking at least a portion of the outer thread on the outer surface of the protrusion with a mating feature on a collar of the male needleless connector when the collar is received within an outer portion of the second cavity (40, 140, 240).

In one or more embodiments, an inner portion of the second cavity (40, 140, 240) can extend further into the housing toward the top wall than an outer portion of the second cavity (40, 140, 240). In one or more embodiments, the profile of the inner thread can be essentially parallel to, or coincide with, a profile of the outer thread.

In one or more embodiments, the inner thread and outer thread can include an inclined thread pattern. In one or more embodiments, the inner thread and outer thread can include a helical-shaped thread pattern. In one or more embodiments, the inner thread or the outer thread can include one or more gaps in the thread pattern.

In one or more embodiments, the inner surface of the protrusion can be essentially parallel to the outer surface of the protrusion.

In one or more embodiments, at least one disinfection sponge is configured within the second cavity (40, 140, 240).

In one or more embodiments, the cap can include a removable cover sealing the opening to the second cavity to seal the disinfection sponge within the second cavity prior to use of the cap.

Figure 50:
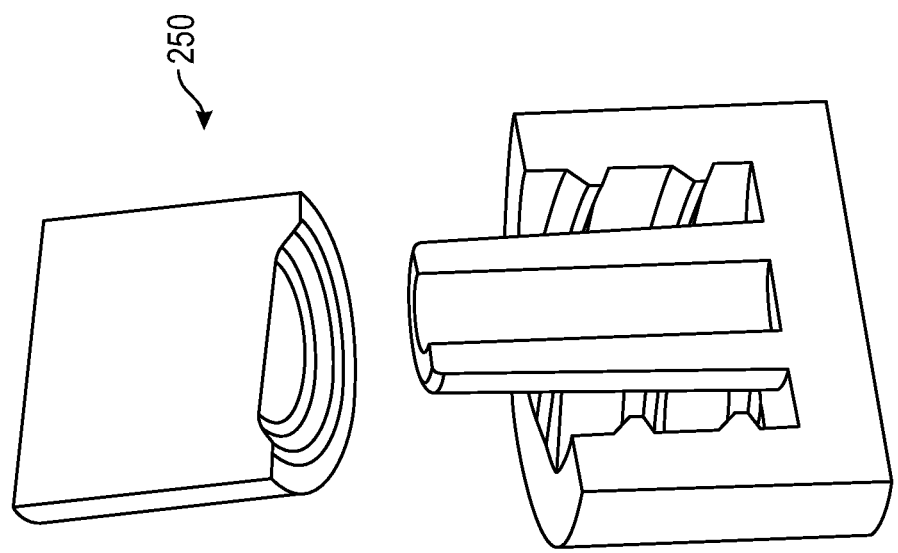
FIG. 50 illustrates a cross-sectional view of an exemplary sealing sponge positioned over tip of an exemplary medical connector according to one or more embodiments of a third aspect of the disclosure.
Figure 49:
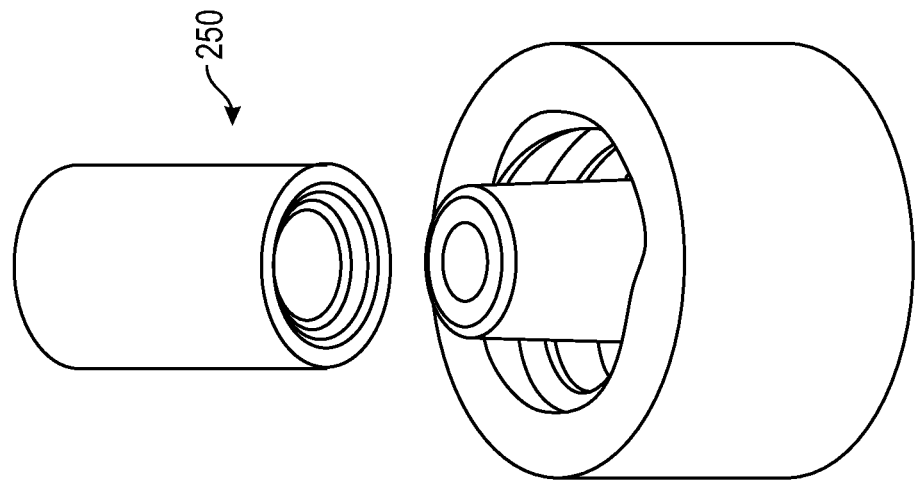
FIG. 49 illustrates a perspective view of an exemplary sealing sponge positioned over tip of an exemplary medical connector according to one or more embodiments of a third aspect of the disclosure.

In one or more embodiments, the absorbent material 250 can be configured within the second cavity 240. As shown in FIGS. 49 and 50, the top surface of absorbent material 250 has a dimpled opening that is contoured to accommodate a tip of a medical connector when positioned over the tip of a corresponding male or female medical connector. In one or more embodiments, the disinfectant or antimicrobial agent disinfects an outer surface and an inner surface of the female needleless connector or male needleless connector when the female needleless connector or male needleless connector is inserted into the second cavity 240. In one or more embodiments, as shown in FIG. 43B, septum 262 can be attached to the open bottom of the insert adjacent to dimpled opening of the top surface of absorbent material 250 thereby forming a seal for maintaining the disinfectant or an antimicrobial agent within the second cavity 240 prior to use of the cap 210. In one or more embodiments, the absorbent material 250 can be a foam or a sponge. In one embodiment, the foam can be a polyurethane foam. In one or more embodiments, the absorbent material 250 can include slits. In one or more embodiments, a compression of the absorbent material 250 toward the top wall of the housing occurs upon connection to the female needleless connector, whereby compression of the absorbent material disinfects the female needleless connector. In one or more embodiments, the absorbent material 250 can be under radial compression by the inner thread on the inner surface of the split-thread protrusion to retain the absorbent material in the second cavity. In one or more embodiments, absorbent material 250 is a closed cell foam sponge with surface roughness and geometry features that is effective for sealing off the fluid path opening in IV Luer Connectors when a disinfecting cap 210 is applied. Sealing the connectors when a disinfecting cap is applied is a particular advantage for a disinfecting cap 210 because: 1) the sealing effect of the absorbent material and/or septum limits the amount of disinfecting solution from ingressing into the fluid path opening in an IV Luer Connector; and 2) the sealing effect of the absorbent material and/or septum limits the amount of leakage of the fluid in the luer connector and the IV line it is attached to, from leaking out, in the event that the intravenous line clamp or valve is inadvertently left in the open state, when a disinfecting cap is applied to the luer connector.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

In some embodiments, the connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). In some embodiments, the cap can be connected with any of a variety of different needleless injection sites, such as those previously listed. In one or more embodiments, after the cap has been coupled with a connector, it is unnecessary to disinfect (e.g. treat with an alcohol swab) the connector prior to each reconnection of the connector with another connector, as the connector will be kept in an uncontaminated state while coupled with the cap. Use of the cap replaces the standard swabbing protocol for cleaning connectors.

A fourth aspect of the present disclosure pertains to a method of disinfecting a medical connector. The method comprises connecting the cap of one or more embodiments to a medical connector, wherein connecting includes engaging the threads of the medical connector onto the threads on the inner or outer surface of the second cavity of the cap upon insertion of the medical connector into the cap such that the medical connector contacts the absorbent material and the disinfectant or antimicrobial agent.

The exemplary caps (10, 110 and 210) of the present disclosure are capable of continuous disinfection of a connector and minimize ingress of microbial agents.

Disinfecting caps currently on the market are capable of only disinfecting one of the three types of luer fitting, namely female luer of needle-free connectors, female luer of stopcocks, and male luer connectors on intravenous injection sites. Thus, to avoid having to use different types of disinfecting caps to clean different types of connectors, exemplary caps (10, 110 and 210) engages with male luer connectors and also with female luer connectors thereby allowing the user to clean different types of connectors with a single device. Upon mounting exemplary caps (10, 110 and 210) onto female luer connectors, the female luer connectors is inserted into the second cavity (40, 140, 240) and screwed onto the inner threads (36, 136, 236) of the exemplary caps (10, 110 and 210). Upon mounting the cap onto a male luer connector, the male luer connector is inserted into the second cavity (40, 140, 240) and screwed onto the outer threads (38, 138, 238) of the exemplary caps (10, 110 and 210). The absorbent material (50, 150, 250) and the disinfectant or the antimicrobial agent contacts the female luer connector after insertion of the female luer connector into the second cavity (40, 140, 240) of the exemplary caps (10, 110 and 210). The absorbent material (50, 150, 250) and the disinfectant or the antimicrobial agent contacts the male luer connector, the female luer connector, and the hemodialysis connector after insertion of the connector into the second cavity (40, 140, 240) of the exemplary caps (10, 110 and 210).

Hence, the device of the present disclosure can be mounted onto both male and female luer connectors, thus fulfilling a current need in the art.

A fifth aspect of the present disclosure pertains to an assembly. The assembly comprises the cap of one or more embodiments connected to a medical connector. In one or more embodiments, the medical connector is selected from a male luer connector, a female luer connector, and needleless connector.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. An assembly comprising:
   a medical connector; and
   a cap having a housing with a top wall, a sidewall forming a first cavity, and an open bottom formed by said sidewall with an opening to the first cavity within said housing for receiving a hub of a medical connector, a protrusion positioned within said first cavity of the housing, the protrusion having an inner surface and an outer surface, the inner surface of the protrusion defining a second cavity, an inner thread on said inner surface of the protrusion, and an outer thread on said outer surface of the protrusion.

2. The assembly of claim 1, wherein the medical connector is a male luer connector, a female luer connector, or needleless connector.

3. The assembly of claim 2, wherein when a hub of a male needleless connector is received within said inner surface of said second cavity, said hub is secured within said first cavity by interlocking at least a portion of said outer thread on said outer surface of the protrusion with a mating feature on a collar of said male needleless connector when said collar is received within an outer portion of said second cavity.

4. The assembly of claim 2, wherein when a hub of a female needleless connector is received within said inner surface of said second cavity, said hub is secured within said inner surface of said second cavity by interlocking at least a portion of said inner thread with a mating feature on said hub of said female needleless connector.

5. The assembly of claim 1, wherein said protrusion comprises one or more cantilevered prongs separated by one or more respective gaps.

6. The assembly of claim 1, wherein said protrusion extends essentially from an inner surface of said top wall toward said open bottom of said housing.

7. The assembly of claim 1, wherein said protrusion extends essentially parallel to said sidewall of the housing.

8. The assembly of claim 1, wherein an inner portion of said second cavity extends further into said housing toward said top wall than an outer portion of said second cavity.

9. The assembly of claim 1, wherein a profile of said inner thread is essentially parallel to, or coincide with, a profile of said outer thread.

10. The assembly of claim 1, wherein the inner thread and the outer thread have an inclined thread pattern.

11. The assembly of claim 1, wherein the inner thread and outer thread have a helical-shaped thread pattern.

12. The assembly of claim 1, wherein the inner thread or the outer thread has one or more gaps in a thread pattern.

13. The assembly of claim 1, wherein said inner surface of the protrusion is essentially parallel to said outer surface of the protrusion.

14. The assembly of claim 1, further comprising at least one disinfection sponge configured within said second cavity.

15. The assembly of claim 14, further comprising a removable cover sealing said opening to said second cavity to seal said disinfection sponge within said second cavity prior to use of said cap.

16. The assembly of claim 1, wherein an exterior wall surface of the sidewall of the housing includes a plurality of grip members.

17. The assembly of claim 1, further comprising an absorbent material configured within said second cavity.

18. The assembly of claim 17, wherein the absorbent material has slits.

19. The assembly of claim 18, further comprising a disinfectant or an antimicrobial agent.

20. The assembly of claim 19, wherein the disinfectant or the antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

21. The assembly of claim 1, wherein the protrusion is a split-thread protrusion.

* * * * *